(12) United States Patent
Nijhuis et al.

(10) Patent No.: US 10,461,166 B2
(45) Date of Patent: Oct. 29, 2019

(54) ELECTRICAL CONTACT

(71) Applicant: NATIONAL UNIVERSITY OF SINGAPORE, Singapore (SG)

(72) Inventors: Christian Albertus Nijhuis, Singapore (SG); Albert Wan, Singapore (SG); Li Jiang, Singapore (SG); Suchand Sangeeth Chandramathi Sukumaran, Singapore (SG)

(73) Assignee: National University of Singapore, Singapore (SG)

( * ) Notice: Subject to any disclaimer, the term of this patent is extended or adjusted under 35 U.S.C. 154(b) by 32 days.

(21) Appl. No.: 15/038,035

(22) PCT Filed: Nov. 19, 2014

(86) PCT No.: PCT/SG2014/000546
§ 371 (c)(1),
(2) Date: May 19, 2016

(87) PCT Pub. No.: WO2015/076751
PCT Pub. Date: May 28, 2015

(65) Prior Publication Data
US 2016/0293722 A1 Oct. 6, 2016

Related U.S. Application Data

(60) Provisional application No. 61/906,277, filed on Nov. 19, 2013.

(51) Int. Cl.
*B32B 15/04* (2006.01)
*H01L 29/45* (2006.01)
(Continued)

(52) U.S. Cl.
CPC ........ *H01L 29/45* (2013.01); *B01L 3/502707* (2013.01); *B01L 3/502715* (2013.01);
(Continued)

(58) Field of Classification Search
CPC .......... B81B 2201/07; B81B 2201/058; B32B 15/04; H01L 51/05; H01L 29/45; B81C 1/00095
See application file for complete search history.

(56) References Cited

U.S. PATENT DOCUMENTS 6,645,432 B1 11/2003 Anderson et al.
2003/0214057 A1 11/2003 Huang

OTHER PUBLICATIONS

Nijhuis et al., "Charge transport and Rectification in Arrays of SAM-Based Tunneling Junctions," Nano Letters 10, 3611-3619 (2010).*

(Continued)

*Primary Examiner* — Kregg T Brooks
(74) *Attorney, Agent, or Firm* — Cesari and McKenna, LLP

(57) ABSTRACT

The present invention relates to an electrical contact. In particular, it relates to an electrical contact capable of establishing an electrical contact with a soft material. More particular, the electrical contact comprises (a) a non-Newtonian liquid metal alloy, the non-Newtonian liquid metal alloy is formed in a polymer insulator, wherein the contact surface of the electrical contact that contacts the soft material is a smooth flat non-patterned surface, the surface comprising the non-Newtonian liquid metal alloy sandwiched between the polymer insulator. The microfluidic device comprising the electrical contact and a method for forming the electrical contact are also disclosed.

15 Claims, 20 Drawing Sheets

(51) Int. Cl.
*H01L 51/10* (2006.01)
*H01L 51/00* (2006.01)
*B01L 3/00* (2006.01)
*B81B 7/00* (2006.01)
*B81C 1/00* (2006.01)
*G01N 27/447* (2006.01)

(52) U.S. Cl.
CPC .......... *B32B 15/04* (2013.01); *B81C 1/00095* (2013.01); *H01L 51/105* (2013.01); *B01L 2300/0645* (2013.01); *B01L 2300/0816* (2013.01); *B01L 2400/0415* (2013.01); *B32B 2307/202* (2013.01); *B32B 2307/412* (2013.01); *B81B 2201/058* (2013.01); *B81B 2207/07* (2013.01); *G01N 27/44791* (2013.01)

(56) References Cited

OTHER PUBLICATIONS

Nijhuis et al., "Molecular Rectification in Metal-SAM-Metal Oxide-Metal Junctions," J. Am. Chem. Soc. 131, 17814-17827, with Supplemental Information (Year: 2009).*

Weiss et al., "Influence of Defects on Electrical Characteristics of Mercury-Drop Junctions: Self-Assembled Monothiolates on Rough and Smooth Silver," J. Am. Chem. Soc. 129, 4336-4349 (Year: 2007).*

Nijhuis et al., "Comparison of SAM-Based Junctions with Ga2O3/EGaIn Top Electrodes to Other Large-Area Tunneling Junctions," J. Phys. Chem. C 116, 14139-14150 (Year: 2012).*

Kramer, R. K. et. al.: "Soft Curvature Sensors for Joint Angle Proprioception", 2011 IEEE/RSJ International Conference on Intelligent Robots and Systems, Sep. 25-30, 2011. San Francisco, CA, USA, p. 1919-1926.

PCT International Preliminary Report on Patentability (Chapter 1 of the Patent Cooperation Treaty) (dated May 24, 2016).

PCT International Search Report (PCT Article 18 and Rules 43 and 44) (dated Feb. 10, 2015).

PCT Written Opinion of the International Searching Authority (dated Feb. 10, 2015).

Siegel, A.C. et. al.: "Cofabrication: A Strategy for Building Multicomponent Microsystems", Accounts of Chemical Research, vol. 43, No. 4, Apr. 2010, p. 518-528 Refer to the whole document and in particular to Fig. 6; p. 524 section titled"Electronic Interfacing with Surfaces"; p. 520-521 section Metal-Filled Channels (Microsolidics) p. 520-521; Table 1;Fig. 6b.

* cited by examiner

ELECTRICAL CONTACT

CROSS-REFERENCE TO RELATED APPLICATIONS

This application is the National Stage of International Application No. PCT/SG2014/000546, filed Nov. 19, 2014, which claims the benefit of priority of U.S. Provisional Patent Application No. 61/906,277, filed Nov. 19, 2013, the contents of both being incorporated by reference in their entirety for all purposes.

FIELD OF THE INVENTION

The present invention relates to an electrical contact. In particular, it relates to an electrical contact capable of establishing an electrical contact with a soft material.

BACKGROUND OF THE INVENTION

Many materials based on molecules, biomolecules, polymers, gels, living tissue, etc are so-called soft materials. Such soft materials have found its way into electronic devices known as molecular electronic devices. Commercial applications of such molecular electronic devices are in the form of thin-films in displays, organic light emitting diodes, or bendable devices. Despite these applications, many questions regarding the details of the mechanisms of charge transport across molecules and the molecule-electrode interfaces remain unanswered. Molecular electronic devices that are based on single molecules, or self-assembled monolayers (SAMs), are potentially good test-beds to study charge transport across molecules and the molecule-electrode interfaces at the nano-scale. The fabrication of such devices is challenging because of the difficulty to form macroscopic-scale electrical contacts to the molecules in non-invasive ways, with high reproducibility, and minimum numbers of defects.

To perform accurate physical-organic studies of charge transport across SAM-based tunneling junctions, it is essential to develop fabrication techniques that have ideally no impact to the chemical structure, or surpamolecular structure of the SAMs, and produce the same data across different operators. In reality, experimental approaches produce devices with defects, e.g., induced by surface roughness of the electrodes, phase domain boundaries of the SAMs, or variations in the details of top-electrode or the conditions of the fabrication process, whose electrical characteristics follow certain distributions. The number of the defects, and the distributions they follow, in these junctions depend on a large number of factors which directly depends on the users. Although the fabrication of the top-electrode received by far the most attention, the quality of the junctions depends equally important on the details of the fabrication of the bottom-electrode (the surface roughness depend on the pre-treatment of the target surface, deposition rate of the metal, base-pressure and cleanliness of the deposition chamber, quality of the metal in the crucible), SAM formation (the purity of the thiol-precursor, quality of the solvent, SAM-formation time, rinsing procedures). Some of these factors are perhaps easier to control, and to capture in the experimental section of a scientific report, than others, but all these factors complicate to generate molecular electronics reproducibly.

Further, these soft materials cannot withstand the rough fabrication methods that are need to form electrical contact to them using conventional deposition techniques (metals melt at temperature far above the decomposition temperature of soft-materials, these materials can also not withstand the high vacuum conditions).

Electronic devices based on organic materials already find commercial applications in the form of thin-films in displays, organic light emitting diodes, or bendable devices. The conventional method of forming the electrical contact between the electrode and the organic materials by depositing metal vapor or solid metals on top of these materials typically damages the molecules and limited the yield and the performance of the devices. It is essential to develop new fabrication techniques that have minimal impact to not only the chemical structure, but also to the supramolecular structure of these soft matter.

SUMMARY OF THE INVENTION

In an aspect of the present invention, there is provided an electrical contact for establishing an electrical contact with a soft material, the electrical contact comprising (a) a non-Newtonian liquid metal alloy, the non-Newtonian liquid metal alloy is formed in a polymer insulator, wherein the contact surface of the electrical contact that contacts the soft material is a smooth flat non-patterned surface, the surface comprising the non-Newtonian liquid metal alloy sandwiched between the polymer insulator.

Preferably, the contact surface of the electrical contact that contacts the soft material is controlled by modulating the size of the polymer insulator.

Preferably, the diameter of the non-Newtonian liquid metal alloy is between 15 μm to 55 μm. More preferably, the diameter of the non-Newtonian liquid metal alloy is between 35 μm to 55 μm.

Preferably, the non-Newtonian liquid metal alloy is EGaIn. The EGaIn comprising 75.5 wt % Ga and 24.5 wt % In.

Preferably, the polymer insulator is PDMS and is transparent.

Preferably, the soft material is formed on a metal substrate. The metal in the metal substrate is any one selected from the group: silver, copper, nickel, platinum, palladium and gold.

Preferably, the soft material is purified. Preferably, the organic precursor of the soft material is purified to 99.9% purity.

Preferably, the thickness of the soft material is between 1 nm to 2 nm.

Preferably, the soft material is a self-assembled monolayer of molecules having the formula: $S(CH_2)_{n-1}CH_3$ where n=10, 12, 14, 16 or 18.

In another aspect of the invention, there is provided a microfluidic device, the device comprising: (a) a first microfluidic channel in a first plane, the first channel having an inlet and an outlet; (b) a second microfluidic channel in a second plane and in fluidic communication with the first, the second microfluidic comprising: (i) a first end in communication with the first channel to form a connection; and (ii) a second end opposite the first end to form an outlet, wherein the connection further comprises an outlet for exposing a non-Newtonian liquid metal alloy when the alloy is formed in the first channel.

Preferably, the connection between the first and second channel is intermediate the inlet and outlet of the first channel.

Preferably, the first and second channels are perpendicular to each other.

Preferably, the device is made of a polymer insulator. More preferably, the polymer insulator is a transparent PDMS.

Preferably, the outlet for exposing the non-Newtonian liquid metal alloy is between 15 µm to 55 µm in diameter. The present invention includes any suitable size of the diameter so long as the right combination of materials is used as known to the skilled person.

In another aspect of the present invention, there is provided a method for forming an electrical contact capable of establishing an electrical contact with a soft material, the method comprising: (a) forming a non-Newtonian liquid metal alloy in a polymer insulator, wherein the contact surface of the electrical contact that contacts the soft material is a smooth flat non-patterned surface, the surface comprising sandwiching the non-Newtonian liquid metal alloy between the polymer insulator.

Preferably, the method further comprises modulating the size of the polymer insulator to control the contact surface of the electrical contact.

Preferably, the diameter of the non-Newtonian liquid metal alloy is between 15 µm to 55 µm. More preferably, the diameter of the non-Newtonian liquid metal alloy is between 35 µm to 55 µm.

Preferably, the non-Newtonian liquid metal alloy is EGaIn. The EGaIn comprising 75.5 wt % Ga and 24.5 wt % In.

Preferably, the polymer insulator is PDMS and is transparent.

Preferably, the method further comprises forming the soft material on a metal substrate.

Preferably, the metal in the metal substrate is silver.

Preferably, the soft material is a self-assembled monolayer of molecules having the formula $S(CH_2)_{n-1}CH_3$ where n=10, 12, 14, 16 or 18.

The present invention is a non-destructive way to form electrical contact to soft matter by using a top-electrode of a non-Newtonian liquid metal alloy of a eutectic mixture of 75.5% Ga and 24.5% In by weight (EGaIn; melting point is 15.7° C.; this alloy is also non-toxic) stabilized in a transparent rubber (polydimethylsiloxane; non-toxic PDMS). The electrical contact can be formed by simply stamping the stabilized metal top-electrode on the target surface. The area of the electrical contact can be controlled by modulating the size of the rubber mold. This invention has been tested for self-assembled monolayers (SAMs) that are only 1-2 nm thick, 2D polymers, thin layers of small molecules and nanoparticles. Advantageously, this method was successfully applied by non-experienced users, the top-electrode is stable enough to be posted.

Advantageously, the present invention described here makes it possible to form reliable, reproducible electrical contact to soft-matter without destroying or altering the fragile molecules.

By "soft material", it is meant to include molecules, biomolecules, polymers, gels, living tissue or the like.

By "eutectic mixture", it is meant to include any mixture having a melting point lower than that of any of it components.

By "non-Newtonian fluid", it is meant to include any fluid that exhibits a viscosity or flow behaviour that vary with changing shear stress or shear rate, i.e. the shear rate is a non-linear function of the shear stress. In an embodiment of the present invention, fluid refers to any liquid metal alloy known to the skilled person suitable, for use in preparing electrical contacts in a microfluidic device described in this application. Non-Newtonian fluids may comprise polymers, polymer solutions, emulsions, multiphase fluid mixtures, colloidal suspensions and the like. These non-Newtonian fluids may be useful as pharmaceuticals, adhesives, food products, personal care products, coating compositions, and the like. A problem with treating non-Newtonian fluids in microfluidic channels relates to the fact that when the non-Newtonian fluids flow at high flow rates, high velocity gradients at the walls of the microfluidic channels are created. This leads to high apparent viscosities and high pressure drops within the microfluidic channels. This invention, in at least one embodiment, provides a solution to this problem.

Not all non-Newtonian Fluids behave in the same way when stress is applied—some become more solid, others more fluid. Some non-Newtonian fluids react as a result of the amount of stress applied, while others react as a result of the length of time that stress is applied. Thixotropic (Viscosity decreases with stress over time), Rheopectic (Viscosity increases with stress over time), Shear thinning (Viscosity decreases with increased stress), Dilatant or shear thickening (The viscosity of a shear thickening fluid, or dilatant fluid, appears to increase when the shear rate increases). Bingham plastic—Fluids that have a linear shear stress/shear strain relationship require a finite yield stress before they begin to flow (the plot of shear stress against shear strain does not pass through the origin). These fluids are called Bingham plastics. Several examples are clay suspensions, drilling mud, toothpaste, mayonnaise, chocolate, and mustard. The surface of a Bingham plastic can hold peaks when it is still. By contrast Newtonian fluids have flat featureless surfaces when still.

Also included in the present invention may be pseudoplastic liquids that tend to exhibit a low viscosity under high-stress conditions and a high viscosity under low-stress conditions, showing a negligible yield value and a viscosity that decreases with increasing shear stress.

Other examples of suitable non-Newtonian fluids for use with embodiments of the present invention include:

Polyacylamide or polyacrylamide-co-acrylate in water. Suitable concentrated solutions of polyacrylamides or partially hydrolyized polyacrylamides are commercially available under the Dow Chemical.

Polyacrylic acid in water (e.g., nominal concentration in the range of 1 to 2000 ppm).

Carboxymethylcellulose, carboxyethylcellulose, carboxypropylcellulose, or other compounds in the carboxylated-cellulose family in water (e.g., nominal concentration in the range of 2 to 2000 ppm). Suitable concentrated solutions of carboxylated-celluloses are commercially available under the Hercules trademarks AQUALON and NATROSOL.

Xanthum gum in water (e.g., nominal concentration in the range of 20 to 2000 ppm).

Hydoxymethylcellulose, hydroxyethylcellulose, hydroxypropylcellulose, or other compounds hydroxylated-cellulose family in water (e.g., nominal concentration in the range of 20 to 2000 ppm). Suitable concentrated solutions of hydroxylated-celluloses are commercially available under the Hercules trade name AQUALON.

Polyethylene oxide in water (e.g., nominal concentration of 0.1 to 2.5% by weight).

Hydroxypropyl starch phosphate in water (e.g., nominal concentration of 0.1 to 2.5% by weight). Suitable concentrated solutions are commercially available under the National Starch trade name Structure ZEA.

This list is not exhaustive, however, and any of a wide variety of non-Newtonian fluids could be used so long as the fluid is electrically conductive. Other types of liquid metal alloys that may be used include: Galistan, any low melting point solders, pure Galium, or any other variations of Galium and Indium alloys that contain a third component (for example, Tin).

The ability to inject metal into microfluidic channels is important for the co-fabrication of low-cost, flexible electronic components such as microscale wires, circuit elements, electrodes, and electromagnets. We show here that EGaIn i) rapidly flows into and fills microfluidic channels at RT when a critical pressure—the value of which depends on the geometry of the channel—is applied to the inlet of the channel, and ii) maintains structural stability (i.e., does not spontaneously retract from the channel) when this pressure is relieved. In some applications, EgaIn may have an advantage over molten solders (used in a set of methodologies called "microsolidics"), which require heating and cooling steps that increase the time needed for the fabrication process, and make it incompatible with heat sensitive materials such as organics.

EGaIn is a liquid metal alloy with the following attributes:

i) EGaIn is electrically conductive. This property allows EGaIn to be used as a contact electrode for the electrical characterization of thin-film organic and semiconductor devices.

ii) The surface of EGaIn is covered with a thin "skin". The skin is apparent to the un-aided eye when a drop of EGaIn is placed on a substrate and the substrate is tilted. The gravitational forces cause the EGaIn to redistribute (i.e. flow) underneath the confines of the skin.

iii) EGaIn is moldable—which is the ability to shape a material into free-standing, stable structures in which the surface free energy is not minimized. Its moldability may be a function of the ratio of surface area to volume (a ratio which increases as the size of the structure decreases), and is therefore attributable to the properties of its skin.

iv) EGaIn is a low-viscosity fluid in the absence of the skin. This low viscosity allows it to be used as an electrically conductive, thermally stable lubricant, and explains why it flows readily—within the confines of its skin—when a drop is placed on a tilted substrate made the channels out of PDMS using standard soft lithography techniques because these techniques are simple and widely used (and therefore easily adaptable by others).

This present invention describes a method to construct tunnel junctions based on self-assembled monolayers (SAMs) by forming reversible electrical contacts to SAMs using top-electrodes of a non-Newtonian liquid-metal (GaOx/EGaIn) stabilized in a microfluidic-based device. Advantageously, a single top-electrode can be used to form up to 15-25 junctions. This method generates SAM-based junctions with highly reproducible electrical characteristics in terms of precision (widths of distributions) and replicability (closeness to a reference value). The reason is that this method, unlike other approaches that rely on cross-bar or nano/micropore configurations, does not require patterning of the bottom-electrodes and is compatible with ultra-flat template-stripped (TS) surfaces. This compatibly with non-patterned electrodes is important for three reasons. i) No edges of the electrodes are present at which SAMs cannot pack well. ii) Patterning requires photoresist that may contaminate the electrode and complicate SAM formation. iii) TS-surfaces contain large grains, have low rms values, and can be obtained and used (in ordinary laboratory conditions) within a few seconds to minimize contamination. The junctions have very good electrical stability (2500 current-voltage cycles and retained currents for 27 h), and can be fabricated with good yields ($\approx$78%).

This technique to form electrical top-contacts to SAMs (that are only 1-2 nm thick) relies on a top-electrode of a non-Newtonian liquid metal alloy stabilized in PDMS. This top-electrode can be directly stamped on to the SAMs, removed from the SAMs once the measurements are completed, and used again to from a new junction up to 15 times. Thus, this method provided the opportunity to investigate the electrical characteristics of SAM-based junctions fabricated by different users operating the same top-electrode, to obtain complete beta-plots, i.e., the current measured at 0.50 V vs the number of carbons in a series of alkanethiols of $S(CH_2)_{n-1}CH_3$ with n=10, 12, 14, 16, and 18, for a single top-electrode. We found that the electrical characteristics are highly reproducible between different users and top-electrodes and the junctions have very good stabilities.

In general, the junctions have good electrical stability (2500 J(V) curves or applying DC bias for 27 h did not damage the junctions), and high yields in working junctions (around 80%). The fabrication of the junctions was performed in ordinary laboratory conditions and does not require clean room conditions or elaborated fabrications steps involving lithography for instance (the fabrication of the molds to shape the PDMS does require clean room conditions). This technique is compatible with template-stripped bottom-electrodes and does not require patterning of the bottom-electrode which ensures that the electrodes that support the SAMs are clean and never had been exposed to—often difficult to completely remove—photoresist, and also avoids edges of the electrodes at which SAMs cannot pack well. The stabilization of the top-electrode minimizes the user-to-user variation in the formation of the top-electrodes, defines the geometric area of the junctions, and minimizes the potential error associated with cone-shaped tips of EGaIn suspended from a syringe such as vibrations, pressure at which the tip is brought in contact with the SAM, or drift of the tip with respect to the SAM. Prior to SAM formation we purified the thiols. All these factors resulted in very narrow log-normal distributions of the values of J ($\sigma_{log}$=0.12–0.25) and excellent reproducibility between different users and batch-to-batch junctions. Although the details of the electrodes are important in junctions, we wish to emphasize that all other factors, for instance, the roughness of the bottom-electrodes or the quality of the SAMs, are of equal importance to obtain highly reproducible junctions.

Our method yield junctions with values of $\beta$=1.0 $n_C^{-1}$ (which is the consensus value of $\beta$—an important electrical parameter) in combination of high yields (nearly 80%) in working devices and the smallest error ($\sigma_{log}$=0.18; Table 2). Only a few other methods generate junctions with higher yields in working junctions, but do so with smaller values of $\beta$ or large value of $\sigma_{log}$. Many fabrication methods use protective layers (to protect the SAMs during the metal deposition process to form the top-contacts) that are deposited by solution based processes, or on the deposition of the electrode from solution (Table 2). We believe that this method to form electrical contacts to SAMs of n-alkanethiolates can be readily extended to other types of SAMs, monolayers of biomolecules, or other types of materials that may not be compatible with direct deposition methods of metals, or exposure to solvents, to form high quality junctions in good yields with high reproducibility.

BRIEF DESCRIPTION OF THE FIGURES

In order that the present invention may be fully understood and readily put into practical effect, there shall now be described by way of non-limitative examples only preferred embodiments of the present invention, the description being with reference to the accompanying illustrative figures.

In the Figures.

DETAILED DESCRIPTION OF THE PREFERRED EMBODIMENTS

Figure 1:
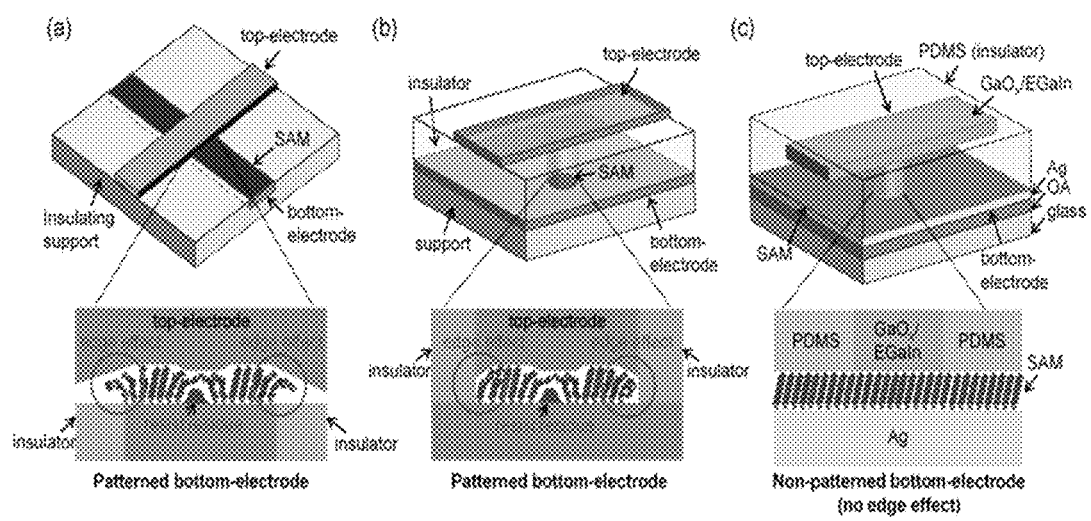
FIG. 1 is a schematic diagram showing a comparison of the molecular junction according to an embodiment of the present invention with other molecular junctions.

The present invention relates to a method to fabricate SAM-based tunnel junctions that generate highly reproducible J(V) data in terms of precision and accuracy, in good yields of working junctions, with a value of the tunneling decay coefficient β close to the consensus value, and good electrical stability. This method works well because it i) does not require patterned bottom-electrodes, ii) is compatible with ultra-flat template stripped bottom-electrodes that contain large grains, iii) does not expose the SAMs to harsh fabrication conditions, and iv) minimizes potential contamination of the bottom-electrode from the ambient. These improvements in the fabrication process resulted in SAM-based junctions of high quality and reproducibility that are (nearly) independent of the users or top-electrodes.

By far most studies have focused to develop techniques to maximize yields of working junctions, or to produce them on large scales, but the reproducibility of the systems has been rarely defined and reported. It is well-known that some electronic properties of SAMs have been reproduced across several test-beds, but with a large spread in the current densities of eight to nine orders of magnitude. The width of the distributions indicates the precision of the data. The closeness of the average value of the distribution to a reference value, or standard value, indicates the accuracy (see FIG. 2). Standards for electrical characteristics across test-beds have not been defined because often standards have not been established within a single laboratory or, for a given technique, across different laboratories.

It has been reported that clean template-stripped (TS) metal surfaces are ultra-flat (three to four times lower rootmean-square (rms) surface roughness than the surfaces fabricated by direct metal deposition) and readily available in ordinary laboratory conditions: the metal surface can be stripped off the template and immediately (within a few seconds) immersed into a solution with the SAM precursor to minimize contamination from the ambient environment. It has been shown that these TS metal surfaces resulted in SAM-based junctions in higher yields and a smaller spread in the J(V) data than those junctions formed with bottom-electrodes obtained by direct metal deposition. Hence, a fabrication technique to construct SAM-based devices that is compatible with TS surfaces, that is, a technique that does not require patterning of the bottom-electrode, is highly desirable.

Cone-shaped tips of a liquid-metal alloy (eutectic mixture of 75.5% Ga and 24.5% In by weight with a thin 0.7 nm surface layer of conductive GaOx, abbreviated as GaOx/EGaIn) have been used to form electrical contacts to SAMs in various physical-organic studies of charge transport across SAMs. This method produces highly reproducible data in good yields and is very easy to set-up in a laboratory. This method has also disadvantages and it suffers from user dependent variations in the details of the formation of tips and the SAM//GaOx/EGaIn contacts, and the stability of the junctions is limited by the details of the micromanipulator on which the top-electrode is mounted.

Here we describe a new type of top-electrode that allows us to form molecular junctions without the need for patterning of the bottom-electrode that is compatible with metal surfaces obtained by TS (as shown in FIG. 1c). As shown in FIG. 1(c), The GaOx/EGaIn (10) was stabilized in a microfluidic device (15) made of a transparent rubber of polydimethylsiloxane (PDMS) (20), which acts as an insulator, which we placed on the self-assembled monolayer of molecules SAMs (25). After electrical examination of the junctions, we removed the top-electrode (30) from the SAM (25) and placed it in contact with a different area of the SAM, or with a SAM on a different substrate (35), to form a new junction. Our method produces J(V) data that are very similar to data obtained by other EGaIn-based techniques, and are independent of temperature, from which we conclude that coherent tunneling dominates the mechanism of charge transport (see Table 1).

TABLE 1

The average values of log|J|, β, and $J_0$, measured using different EGaIn-based techniques for n-alkanethiolate SAMs.

| Techniques | <log|J|> [A cm$^{-2}$] | | | | | β [$n_C^{-1}$] | $J_0$ [A cm$^{-2}$] |
|---|---|---|---|---|---|---|---|
| | $SC_9CH_3$ | $SC_{11}CH_3$ | $SC_{13}CH_3$ | $SC_{15}CH_3$ | $SC_{17}CH_3$ | | |
| this work | −1.95 | −2.92 | −3.63 | −4.63 | −5.44 | 1.00 ± 0.03 | 2.4 × 10$^2$ |
| tips[a)] | −1.77 | −2.47 | −3.70 | −4.32 | −5.31 | 1.02 ± 0.09 | 3.4 × 10$^2$ |
| modified tips[b)] | −1.250 | −1.60 | −2.30 | −3.270 | −4.10 | 0.91 ± 0.02 | 25 × 10$^2$ |
| cross-bar[c)] | NA | −2.70 | −3.20 | −4.50 | −5.20 | 0.92 ± 0.24 | 3.4 × 10$^2$ |
| Reference values[d)] | −1.7 ± 0.4 | −2.4 ± 0.6 | −3.2 ± 0.6 | −4.2 ± 0.6 | −5.0 ± 0.6 | 1.00 ± 0.02 | 0.2-2 × 10$^3$ |

Figure 5:
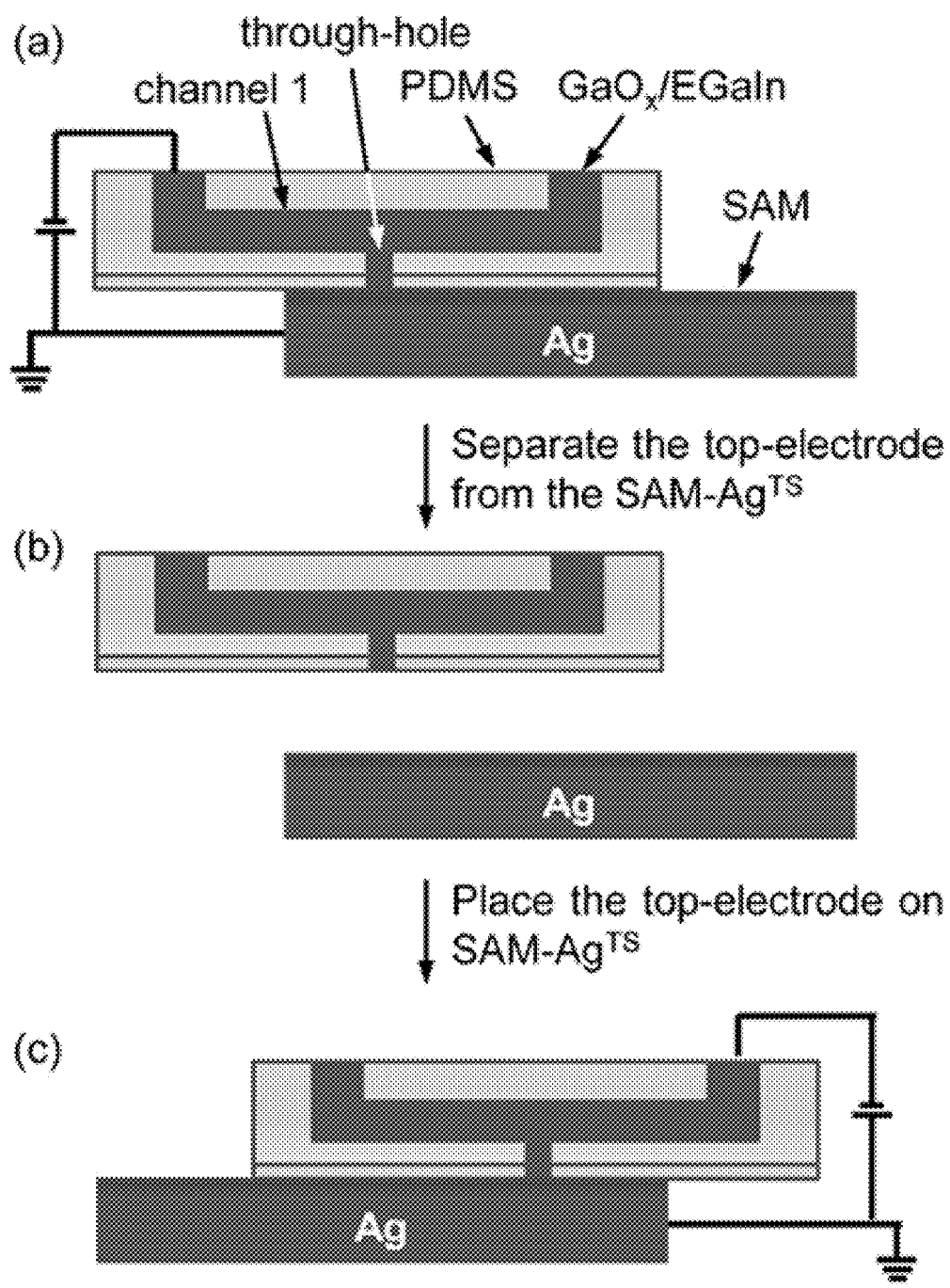
FIG. 5 is a schematic diagram showing the electric contact according to an embodiment of the present invention.

As such, as can be seen in FIG. 1(c), an electrical contact such as an electrical contact (30) can be fabricated and prepared for establishing an electrical contact with a soft material such as SAMs (25). The SAMs may be one cell thick (about 1 nm to 2 nm in thickness), and may be purified by any techniques known to the skilled person. Such an electrical contact may be known as a top-electrode (30) comprising a non-Newtonian liquid metal alloy (10) that is formed in a polymer insulator (20). In the embodiment of the present invention, the alloy used is GaOx/EGaIn. As described above, any liquid metal alloy that has conductive properties may be used. From a side view of the device (15), the liquid metal alloy (10) is formed such that it is sandwiched between two portions of the polymer insulator (20) to form a smooth flat non-patterned surface that contacts the soft material SAM (25). The SAM (25) is formed on an Ag substrate (35) to form a bottom-electrode (40). The advantage of the smooth flat surface is that, unlike other electrical contacts shown in FIGS. 1(a) and 1(b), there is no "edge effect"—a disadvantage described above. FIG. 5 shows the electrical contact in use—contact between top electrode and bottom electrode.

The sandwiched portion of the liquid metal alloy (10) may be any suitable diameter. In the present invention, the diameter may be between 15 μm to 55 μm. The amount of liquid metal alloy (10) in relation to the amount of polymer insulator (20) sandwiching it may be any amount a skilled person may find suitable to achieve the electrical characteristics of the electrical contact (30) which will be described in detail below.

In an embodiment of the present invention, the polymer (or rubber) insulator (20) is a transparent PDMS. The liquid metal alloy (10) may be any non-Newtonian liquid metal alloy. In the present case, the alloy is a eutectic mixture of Ga and In (EGaIn) comprising 75.5 wt % Ga and 24.5 wt % In. The substrate (35) may be silver, copper, nickel, platinum, palladium or gold.

The advantages of the present method is that encapsulation of the metal top-electrodes in PDMS eliminates instabilities associated with micromanipulators, e.g., drift or vibrations, and minimizes user-to-user variations in the details of the formation of the top-electrode and the SAM// GaOx/EGaIn contacts resulting in data with high precision and replicability. These features made it possible to study the electrical characteristics of the junctions over a period of time of ten days, bias stressing up to 1.0×10$^5$ s, and over the range of temperatures of 160-297 K. Cone-shaped tips of GaOx/EGaIn can only be prepared one at a time per "EGaIn-set-up", while the fabrication process reported here can be performed in parallel to fabricate large numbers of junctions.

EXAMPLE

Junctions with GaOx/EGaIn Top-Electrodes

The EGaIn spontaneously forms a self-limiting layer of GaOx in air with a thickness of 0.7 nm and because of its non-Newtonian properties this material can be shaped. Therefore, unlike Hg, GaOx/EGaIn forms stable structures in PDMS micro-channels. The oxide layer also prevents the bulk EGaIn from alloying with the gold or silver bottom electrode which adds stability to junctions. The oxide layer is defective and contains oxygen vacancies, and it is highly conductive.

The precision of the data, that is, the width of the distributions of the values of J (see FIG. 2 for definitions), generated using junctions formed with cone-shaped tips of GaOx/EGaIn relies on the operator because the formation of the tips and bringing the tip in contact with the SAMs are usually performed with a manually operated manipulator. (Alternatively, piezo-controlled manipulators may be used.) For instance, the contact size, tip roughness, and the speed of the tip used to approach the SAMs, differ in details from user-to-user. It has been shown that these factors broaden the distributions of the current densities significantly. Recently, it was reported that flattening the cone-shaped tips by molding the tips against flat and clean Si/SiO$_2$ surfaces followed by voltage cycling (three cycles of ±2 V) resulted in smoother tips and higher reproducibility between users than using unmodified cone-shaped tips of GaOx/EGaIn. Stabilization of the GaOx/EGaIn in a micro-channel in a cross-bar configuration resulted in well-defined geometrical contact areas, but the improvement in the width of the distributions of the values of J was only marginal because the bottom-electrodes contained edges at which SAMs cannot pack well.

Despite the (small) differences between the details of the formation of the GaOx/EGaIn top-contacts, Table 1 shows that the J(V) characteristics of SAM-based junctions with GaOx/EGaIn top-electrodes across laboratories differ slightly (less than one order of magnitude) compared to the eight to nine orders of magnitude difference in J(V) characteristics across test-beds. Thus "EGaIn"—based techniques produce data that are replicable (in spite of the different levels of precision) across laboratories and platforms.

Precision and Accuracy

According to Equation (1) (see below), the values of log|J| are normally distributed when the error in d follows a normal distribution because J depends exponentially on d. The error in d certainly depends on many factors including defects in the electrode materials, for example, step edges, vacancy islands, or grain boundaries, defects in the SAMs, for example, phase domains, physisorbed or chemisorbed materials, or errors during the fabrication process, for example, (partial) penetration of the SAMs by the top-electrode, or damage to the SAMs inflicted by solvents or high temperatures during fabrication. These potential defects that result in uncertainties in the effective values of d and all may result in batch-to-batch or user-to-user variations and consequently introduce error that cause the data to deviate from Gaussian distributions and increase the standard deviation. Thus, one way to compare the precision of different techniques for junction measurements is to compare the standard deviations ($\sigma$) of the values of J for normal distributions, or the analogues log-standard deviations ($\sigma$ log) for log-standard distributions (see FIG. 2). Data that follow narrow distributions make it possible to separate informative data from non-informative data more accurately than those data that follow broad distributions.

Figure 2:
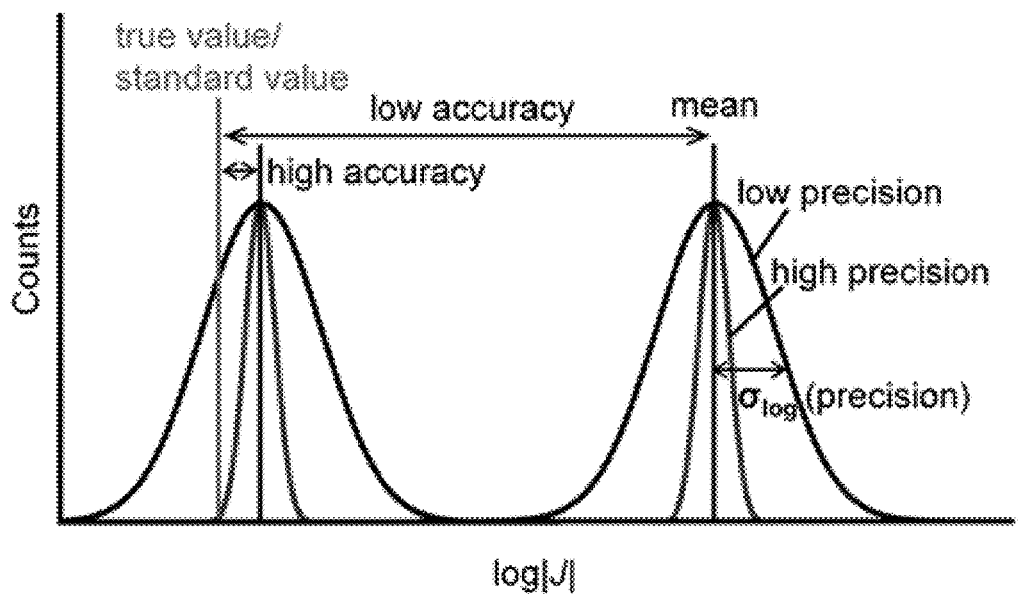
FIG. 2 is a schematic diagram showing the definition of the accuracy and precision of the electrical measurements for SAM-based junctions.

As shown in FIG. 2, the accuracy of the data is defined as the difference between the data obtained from the measurement and the true, or defined, value. This Figure shows that data may be very precise but not accurate, but all other combinations are also possible and, for instance, data may be accurate but not precise. Although the width of the histograms of the values of J may be very narrow for a given test-bed, they do so with values that differ by eight to nine orders of magnitude across different test-beds. In the present invention, we do not aim to define the standards for the absolute values of $J_0$ for junctions with SAMs of n-alkanethiolates because the factors that contribute to $J_0$ for a given test-bed have, in general, not been identified. Here we wish to establish the replicability of our method relative to "EGaIn"-based techniques using reference values of the current densities (Table 1). This comparison helps to identify sources of error that are important to consider in general to maximize both precision and replicability (see below).

Error Analysis

As mentioned above, normally the values of log|J| (for a given voltage) are plotted versus n C followed by fitting this data to the Simmons equation. Previous work included the comparison of compared different statistical methods to determine the values of $\beta$ and $J_0$ and the differences and limitations of these methods thoroughly discussed. These methods either used average values of log|J| (Gaussian mean, median, or arithmetic mean) to which a line was fitted using a least-squares fitting algorithm, or by plotting all data to which a line is fitted using either a least-squares algorithm or by minimizing the sum of the absolute error. Here we chose two methods to determine the values of $\beta$ and $J_0$: i) plotting the Gaussian means of the value of log|J| vs $n_C$ followed by least squares fitting of Equation 1 (method 1) and ii) plotting all data (all values of log|J| except data that was obtained for junctions that shorted) followed by fitting to Equation (1) by minimizing the sum of the absolute values of the error (method 2). The first method assumes the data follow random distributions, or, in other words, the data are normally distributed, while the second method does not make any assumptions regarding the type of distribution.

Results and Discussion

1. Fabrication of the Top-Electrode

Figure 3:
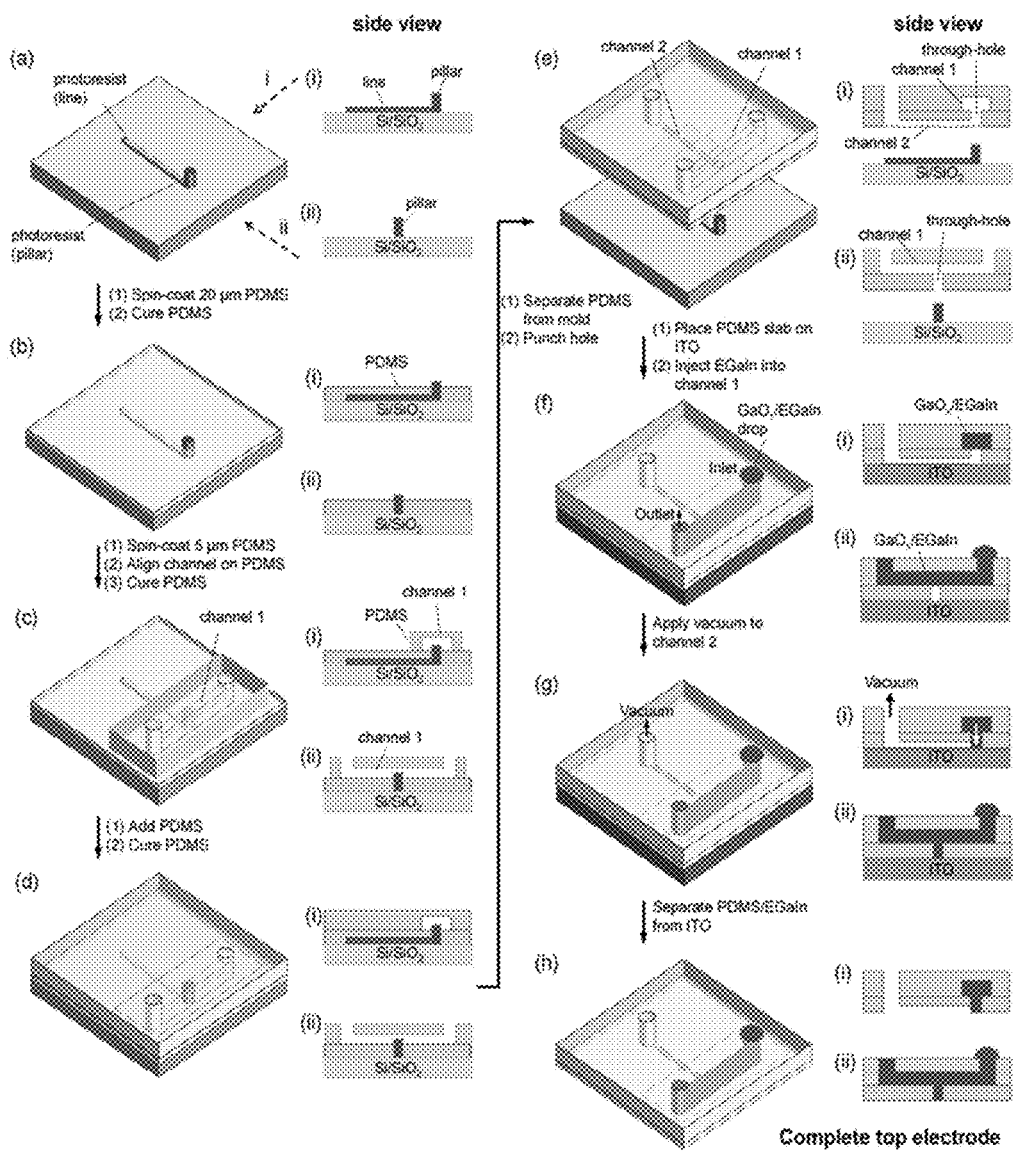
FIG. 3 is a schematic diagram showing the fabrication of a top-electrode according to an embodiment of the present invention.
Figure 4:
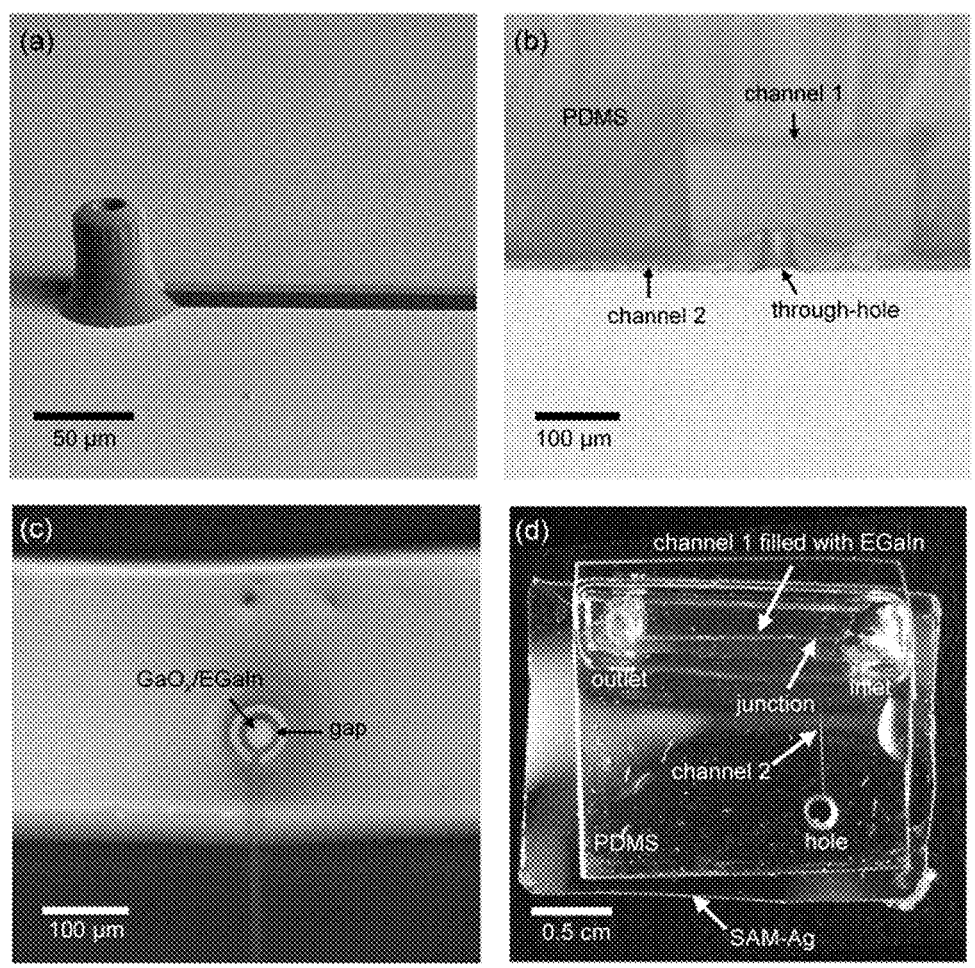
FIG. 4 shows SEM images of the microfluidic device according to an embodiment of the present invention.

In essence, we first fabricated the 3D microfluidic channel and then injected the liquid metal into the channel to complete the formation of the top-electrode. The procedures of fabricating the microfluidic device as the top electrode is shown in FIG. 3. The mold which consists of a line and a pillar made of photoresists on a Si/SiO$_2$ wafer (85), as shown in FIG. 4.

The fabrication process is described in detailed below. Briefly, PDMS was spin-coated on the mold to fully cover the photoresist line, but not over the pillar. A channel in PDMS was aligned over the pillar perpendicularly with respect to the thin channel with the assistance of a thin layer of uncured PDMS as the "glue". More uncured PDMS was added to stabilize the thin layer of PDMS. The microfluidic device was peeled off from the mold and a hole was punched at the end of the small channel (the connection). The width of this small second microfluidic channel was controlled to be smaller than 10 µm to prevent the injection or diffusion of GaO$_x$/EGaIn into this channel. We then place the microfluidic device on an ITO substrate (90) and injected GaO$_x$/EGaIn into the PDMS channel. The outlet of the second microfluidic channel or through-hole (>20 µm) was filled with GaO$_x$/EGaIn by applying vacuum to the small channel. Separation of the microfluidic device from the ITO yielded a complete top-electrode. The electrical contact between the top-electrode and the soft material or matter can be formed by simply placing the top-electrode on the soft material or matter.

The final product of the microfluidic device having an electrical contact according to an embodiment of the present invention is shown in FIG. 3(*h*). The device comprising a first microfluidic channel (channel 1-50) having an inlet (55) and an outlet (60); and a second microfluidic channel (channel 2-65) in a plane that is lower than the plane of channel 1. Both first and second microfluidic channels are in fluid communication with each other. The second microfluidic channel (channel 2-65) further comprising a first end in communication with the first microfluidic channel (channel 1-50) to form a connection (through-hole 70); and a second end opposite the first end to form an outlet (75). The connection (through-hole 70) further comprises an outlet (80) for exposing the liquid metal alloy (10) when the alloy (10) is formed in the microfluidic channel 1. The diameter of the outlet (80) may be between 15 µm to 55 µm.

From the figures in FIG. 3, it can be seen that microfluidic channels 1 and 2 (50 and 65) on different plane but are in fluidic communication. The connection (70) is intermediate the inlet (55) and outlet (60) of the first microfluidic channel 1 (50). In an embodiment of the present invention, the microfluidic channels are perpendicular to each other.

The process as set out in FIG. 3 is described in detail below.

FIG. 3 shows the fabrication process of the top-electrode of GaOx/EGaIn stabilized in a microfluidic chip made of PDMS. We fabricated the mold to shape the PDMS which consisted of a pillar (45) (with a height of 60 µm and the diameter of ≈45 µm) connected to a line (42) (1.0 cm×10 µm×10 µm; FIG. 3*a*) via a two-step photolithography process.

In essence, we followed a procedure reported in Kartalov et al. (P. Natl. Acad. Sci. USA 2006, 103, 12280) to fabricate the mold for PDMS microchannel (channel 2) connected with a through-hole (pillar).

Figure 11:
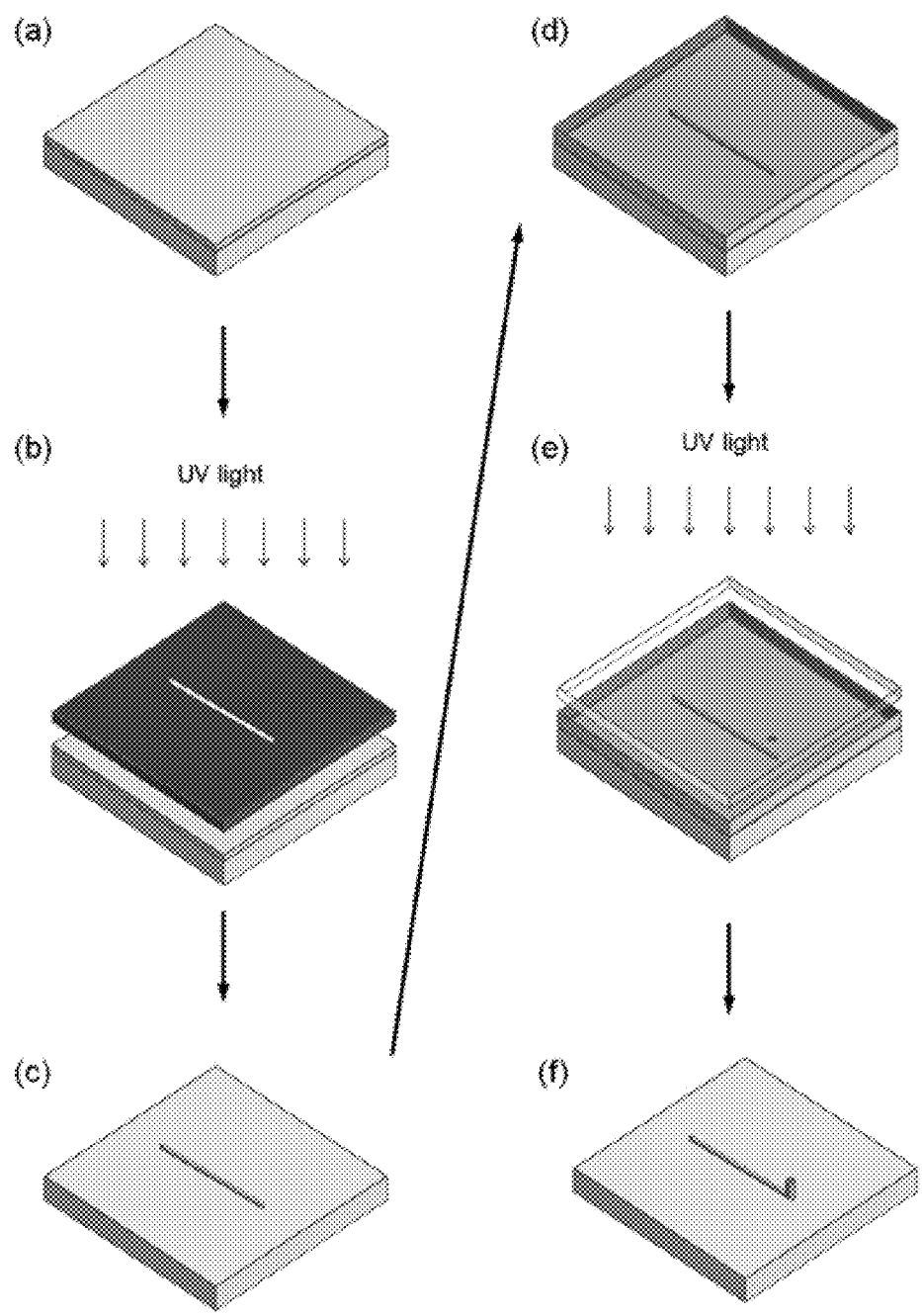
FIG. 11 shows the fabrication steps in the fabrication of the mold for microchannels in PDMS according to an embodiment of the present invention.

The fabrication steps of the fabrication of the mold for micro-channels in PDMS are shown in FIG. 11. In summary, FIG. 11(*a*) shows a SU8-2015 photoresist with thickness of 10 µm was spin-coated on a Si wafer. FIG. 11(*b*) shows that the substrate was exposed to UV light through a photomask. FIG. 11(*c*) shows the unexposed photoresist was removed by developing. FIG. 11(*d*) shows a AZ-50XT photoresist with thickness of 60 µm was spin-coated on the substrate. FIG. 11(*e*) shows that the substrate was covered with another photomask using a mask aligner and exposed to UV light. FIG. 11(*f*) shows the exposed photoresist when removed by developing.

The Si wafer was exposed to hexamethyldisilazane (HMDS) vapor in a bake oven (YES 310TA) at 150° C. for 5 minutes. We deposited 10 µm thick of SU8-2015 photoresist (Microchem) on the wafer by spin-coating the photoresist at 4500 rpm for 1 minute (FIG. 11a). The substrate was baked at 65° C. for 1 minute and 95° C. for 3 minutes on a hotplate. The photoresist was exposed to UV light (5 mW) through a mask for 22 seconds using a mask aligner (Suss Microtech; FIG. 11b), and followed by a post-exposure bake at 65° C. for 1 minute and 95° C. for 3 minutes. After cooling down to room temperature, the structures were developed in SU8 developer (Microchem) to yield a line (FIG. 11c). The substrate was then rinsed with copious amount of isopropyl alcohol, blown to dryness in a stream of N2, and baked at 150° C. for 5 minutes. To form the structure of the pillar at one end of this line, we first deposited 60 μm thick AZ-50XT photoresist (AZ Electronic Materials) by spin-coating the photoresist at 700 rpm for 20 seconds on the wafer with the line-feature, and then baked the substrate for 2, 5, 2, and 9 minutes at 65, 115, 65, and 115° C., respectively (FIG. 11d). The mask was aligned with respect to the wafer followed by exposure to UV light (5 mW) for 2 minutes (FIG. 11e). The substrate was developed in the mixture of 1:1 ratio of AZ 400K developer:water for 5 minutes, and was rinsed with copious amount of water, and blown to dryness with $N_2$ (FIG. 11f).

To fabricate the PDMS channel 1 (that was used to over the pillar), we first fabricated a mold of photoresist with the dimensions of 1.0 cm×300 82 m×120 μm on a Si wafer by spin-coating SU8-3050 at 1000 rpm/s for 1 minute, followed by baking the substrate for 1 and 5 minutes at 65 and 95° C., respectively. The photoresist was then exposed to UV light through a shadow mask with the mask size of 1.0 cm×300 μm. After developing as described above, the resulting mold was treated with FOTS vapor in a vacuum desiccator for 30 minutes. A mixture of 10:1 of PDMS and curing agent was poured on the mold and cured at 80° C. for 1 hour. After curing, we peeled off the PDMS layer from the mold and punched two holes (2 mm) at the ends of the channel 1 prior to alignment over the pillar.

FIG. 4 a shows a scanning electron micrograph (SEM) of the mold. The image shows that the pillar had a larger base-diameter (55 μm) than top-diameter (35 μm) and had a depression at top-center due to over-developing of the thick layer of photoresist during the lithography process.

The fabrication process of the top-electrode of $GaO_x$/EGaIn starts with it being stabilized or formed or cured in a microfluidic device made of PDMS. We fabricated the mold for the PDMS microfluidic chip which consisted of a pillar (with a height of 60 μm and the diameter of 35 μm) connected to a line (1.0 cm×10 μm×10 μm; FIG. 3a). The pillar and the line were made of photoresist by a two-step photolithography process. The mold was treated with 1H,1H,2H,2H-perfluorooctyltrichlorosilane $(Cl_3Si(CH_2)_2(CF_2)_5CF_3$, FOTS) to minimize the interaction of the PDMS with the wafer to ensure the defect free separation of the PDMS from the mold. A layer of 20 μm of uncured PDMS (Sylgard 184) with curing agent (10:1) was formed by spin-coating to fully cover the line but not the pillar (FIG. 3b). After curing of the PDMS at 80° C. for 30 minutes, we formed an addition layer of 5 μm uncured PDMS (with curing agent) on which a channel in PDMS (1.0 cm×300 μm×120 μm), which we fabricated in a separate step, with an inlet and an outlet was aligned over the pillar perpendicularly with respect to the thin line (FIG. 3c). A seal was formed between the layers by curing the 5 μm thick PDMS layer at 80° C. for 30 minutes. This thin PDMS layer prevented air from being trapped between the layers of PDMS and improved the mechanical stability of the devices (which are required to perform measurements as a function of temperature in vacuum; see supporting information). We added more uncured PDMS (with curing agent) with curing agent to stabilize the 20 μm PDMS film (FIG. 3d). After curing the PDMS, we separated the microfluidic device from the mold and punched a hole at the end of the small channel (FIG. 3e). To inject $GaO_x$/EGaIn into the microchannels, we placed the microfluidic device on indium tin oxide (ITO). The transparent and conductive properties of ITO allowed us to follow all subsequent stages of the fabrication process by optical microscopy and conductivity measurements. The large micro-channel was filled with EGaIn by applying vacuum (6~20 Torr) to the outlet of the channel with a drop of GaOx/EGaIn present at the inlet (FIG. 3f). Once the large channel was filled with the liquid metal, we applied vacuum to the small channel to fill the through-hole with $GaO_x$/EGaIn (FIG. 3g). The diameter of the small channel was chosen such that the high surface tension of $GaO_x$/EGaIn prevented it to fill this small channel in the range of the applied pressures. By simply measuring the resistivity between the ITO and the $GaO_x$/EGaIn present at the inlet using a multi-meter we determined if the $GaO_x$/EGaIn filled the through-hole and formed good electrical contacts with the ITO. Examination of the footprint of the contact of the $GaO_x$/EGaIn with ITO by optical microscope allowed us to determine the geometrical area of the contact accurately. Finally, we separated the top-electrode from the ITO (FIG. 3h). During this step, no liquid-metal was left behind on the ITO surface.

From the optical micrographs of FIG. 4, one can see the molds that were used to mold the rubber. Once the mold is prepared it can be used endlessly. FIG. 4(b) shows an optical micrograph of the rubber mold and FIG. 4(c) shows a close up of the small micrometer sized hole without liquid metal and FIG. 4(d) with liquid metal. FIG. 4(a) shows a scanning electron micrograph of the mold recorded from an angle with respect to the surface normal of 60°. The image shows the pillar had a larger base-diameter (70 μm) than top-diameter (40 μm) due to the over-development during the fabrication. FIG. 4(b) shows the optical micrograph of the cross section of PDMS device (without liquid metal in the microfluidic channels) and that the 3D structures of FIG. 4(a) were successfully replicated by the PDMS. We placed the PDMS microfluidic channel on an ITO substrate to monitor the filling of the microfluidic channels with liquid metal. Thus the optical properties of this rubber—the fact that this rubber is transparent—make it possible to follow the fabrication closely and improve yields and reproducibility. FIG. 4 show the optical micrographs before, and after, filling the microfluidic channels with the liquid-metal, respectively. The small channel remained empty because of the high surface tension of the liquid-metal—this small channel is needed to fill the hole. We derived the geometrical contact area of the GaOx/EGaIn with the ITO from these images—again to be able to do so the topical transparent properties of the rubber mold are important.

The mold was treated with 1H,1H,2H,2H-perfluorooctyl-trichlorosilane $(Cl_3Si(CH_2)_2(CF_2)_5CF_3$, FOTS) to minimize the interaction of the PDMS with the wafer to ensure the defect free separation of the PDMS from the mold (see below). A layer of 20 μm of uncured PDMS (Sylgard 184) with curing agent (in a ratio of 10:1) was formed by spin-coating which covered the line but not the pillar (FIG. 3b). After curing of the PDMS at 80° C. for 30 min, we spin coated an additional layer of 5 μm uncured PDMS (with curing agent) and aligned a channel (channel 1) in PDMS (1.0 cm×300 μm×120 μm), which we fabricated in a separate step, with an inlet and an outlet over the pillar perpendicularly with respect to the line of the mold (FIG. 3c). A covalent seal was formed between the layers by curing the 5 μm thick PDMS layer at 80° C. for 30 min. This thin PDMS layer improved the mechanical stability of the devices. We added more uncured PDMS with curing agent to stabilize the 20 μm PDMS film (FIG. 3d). After curing the PDMS, we separated the microfluidic chip which contained two perpendicular channels with a microscale through-hole at the intersection from the mold and punched a hole at the end of the channel 2 (FIG. 3e). FIG. 4b shows the optical micrograph of the cross section of the PDMS device (without liquid metal in the micro-channels) and that the 3D structures were successfully replicated by the PDMS.

To inject GaOx/EGaIn into the micro-channel 1 and the through-hole, we placed the microfluidic chip on indium tin oxide (ITO). The transparent and conductive properties of ITO allowed us to follow all subsequent stages of the fabrication process by optical microscopy and conductivity measurements. Channel 1 was filled with EGaIn by applying vacuum (≈500 Torr) to the outlet of the channel with a drop of GaOx/EGaIn present at the inlet (FIG. 3f), after which we applied vacuum to channel 2 to fill the through-hole with GaOx/EGaIn (FIG. 3g). The diameter of channel 2 was chosen so that the high surface tension of GaOx/EGaIn (624 mN/m) prevented it to fill this channel in the range of the applied pressures. FIG. 4c shows that the liquid-metal did fill the through-hole but not channel 2. We derived the geometrical contact area of the GaOx/EGaIn with the ITO from these images. We found that the diameter of the GaOx/EGaIn-ITO contact (35 μm) was smaller than the diameter of the through-hole (55 μm) because of a gap of ≈10 μm between the GaOx/EGaIn and the walls of the hole. The formation of the gap was likely caused by the high surface-tension of the GaOx/EGaIn. By simply measuring the resistance between the ITO and the GaOx/EGaIn present at the inlet using a multi-meter, we determined if the GaOx/EGaIn filled the through-hole and formed good electrical contact with the ITO. Finally, we separated the top-electrode from the ITO (FIG. 3h). During this step, no liquid-metal was left behind on the ITO surface.

If required, the dimensions of the top-electrodes can be easily reduced by reducing the lengths of channels 1 and 2. As an alternative to the above, a top-electrode with both channels 1 and 2 having a length of 0.5 cm may be fabricated. As a further, alternative, the length of the channels 1 and 2 may be any length between 1.0 to 0.5 cm.

2. Fabrication of the Junctions

FIG. 5 shows schematically the reversible placement of the top-electrode on a SAM on $Ag^{TS}$ electrodes (FIG. 5a).

The figure shows schematically the rubber stamp that stabilizes the non-Newtonian liquid metal. Non-Newtonian liquids behave as solid or liquid depending on the pressure. This liquid metal behave as liquid and can be injected in to microfluidic channels when a pressure difference is applied, but returns to its solid state in ambient conditions. We chose a rubber stamp because this material forms conformal contacts with all target surfaces we tested. The top-panel shows the top-electrode in contact with a monolayer of molecules that are exactly only ONE molecule thick (1-2 nm). The metal is indicated as "GaOx/EGaIn", the rubber is indicated as PDMS, Ag indicate the silver surface that supports the self-assembled monolayer (SAM). The inset show schematically the metal-molecule-metal structure. The panel in the middle show the separation of the top-electrode from the SAM and the bottom panel shows how the electrode is placed back in contact with the target. This step can be repeated up to 20-30 times.

We found that the electrodes formed good electrical contacts with the SAMs in most cases; in cases a good contact did not form (which resulted in either an open circuit or J(V) characteristics with values of J that were more than two orders of magnitude lower than the log-mean value), we simply applied vacuum to channel 2 to restore good electrical contact of the GaOx/EGaIn with the SAM. FIG. 4d shows a photograph of a complete device. The PDMS is flexible and forms a reversible conformal contact with the substrate through van der Waals interactions. We observed that the seal between the top-electrode and the SAM-$Ag^{TS}$ substrate allowed the GaOx/EGaIn to form good electrical contacts with the monolayers. Because the EGaIn surface is exposed to air in our experiments, we believe that the GaOx film that forms spontaneously in air on the bulk metal is continuous and very similar in composition to that in other types of EGaIn-based junctions. After recording the J(V) curves, we separated the top-electrode from the substrate (FIG. 5b), and placed it in contact with the SAM in an area that had not been in contact with either the PDMS (to avoid potential contamination of the SAMs by, for instance, low molecular weight or uncured PDMS) or the GaOx/EGaIn previously, or in contact with another $Ag^{TS}$-SAM substrate (FIG. 5c).

The bottom-electrode (eg. Shown in FIG. 5—with the SAM-AG) may be ultra-flat and/or smooth. It may have a root-mean-square (r.m.s.) roughness around 0.9 nm over an 1×1 μm$^2$ area and large grains (0.2-1 μm$^2$).

The procedure to remove the top-electrode from the surface and to form a new junction typically takes 5-10 s. The rate at which junctions can be formed for a single electrode is similar to that for cone-shaped based techniques (once a cone-shaped tip of $GaO_x$/EGaIn has been formed). We used 4" wafers which allowed us to prepare six top-electrodes at once per wafer, but top-electrodes with shorter channels can also be prepared to yield for instance 18 top-electrodes per wafer. The top-electrodes lasted for about 15-25 junctions before they failed and did not form good electrical contacts with the SAMs. Optical micrographs of these failing top-electrodes revealed that the small channels were blocked by dust particles and therefore good contacts could not be restored by applying vacuum to channel 2. Occasionally (in about 1 out of 20 top-electrodes), the thin PDMS membrane surrounding the GaOx/EGaIn ruptured resulting in ill-defined junction areas. Hence, the number of junctions that can be formed in parallel is only limited by the number of available molds and the rate of data acquisition is only limited by the electronic equipment.

3. Proposed Reference Values of J for EGaIn-Based Techniques

Table 1 shows the values of <log|J|> for $Ag^{TS}$—$SC_n$//$GaO_x$/EGaIn junctions with n=10, 12, 14, 16, and 18. The reference values of <log|J|> were obtained by averaging the values of <log|J|> obtained from earlier and the present work. We determined reference values of β and $J_0$ by least squares fitting the average values of <log|J|> to the Simmons equation (see FIG. 6 and discussion below). The values of $J_0$ depend on many factors, including the effective contact area or contact resistance. Here, we do not aim to compare the absolute values of $J_0$ across test-beds but only across "EGaIn"-based techniques. As we show here, these proposed reference values are useful to compare "EGaIn"-based techniques to each other, or to identify sources of error.

4. The Electrical Characteristics of the Devices

In molecular electronics, it is a common practice to determine the tunneling decay coefficient, ($n_C^{-1}$), by measuring the value of J at a given voltage, V(V), as a function of the thickness of the SAMs, d (Å or $n_C$ which is the number of carbon atoms in the back bone of the molecules), when through bond tunneling is the dominant mechanism of charge transport. By fitting the data to the Simmons equation (Equation (1)), one can derive the values of β and of the hypothetical current density, $J_0$ (A cm$^{-2}$), for a junction with d=0. This procedure has been used across several test-beds using SAMs of n-alkanethiolates of the form $S(CH_2)_{n-1}CH_3$ and it is now commonly believed that the correct value for β is 1.0 $n_C^{-1}$.

$$J = J_0 e^{-\beta d} \quad (1)$$

We formed junctions with SAMs of $S(CH)_{n-1}CH_3$ (n=10, 12, 14, 16, or 18) on $Ag^{TS}$. Prior to the self-assembly of the monolayers, we purified the n-alkanethiolates. Although we did not test the performance of the junctions as a function of thiol purity, this procedure minimizes potential variations in the batch-to-batch quality of the thiols as received from the suppliers which could influence replicability and/or precision of the electrical characteristics of the junctions. Using a single top-electrode, we measured a complete graph of |J| against $n_C$ determined at −0.50 V as follows. We recorded the values of J over the range of biases of −0.50 and 0.50 V (one trace=0 V→0.50 V→−0.50 V (2) 0 V) at intervals of 25 mV. We recorded a total of 20 J(V) traces for each junction and measured three junctions for each type of SAM using a single top-electrode. Thus, we formed 15 junctions with five different SAMs and recorded in total 300 traces and 600 values of |J| at each applied bias using a single top-electrode. This procedure was repeated with five different top-electrodes to yield a total of five plots of versus $n_C$ operated by one out of three different users. This procedure allows us to determine the replicability and precision of data across individual users and top-electrodes.

TABLE 2

The total number of non-shorting junctions ($N_J$), the yields of the working devices and $\sigma_{log}$ of J(V) measurements for the n-alkanethiolate-based junctions.

| Molecules | Junctions | $N_J$ | Non-shorting junctions | Non-shorting yield [%] | $\sigma_{log}$ |
|---|---|---|---|---|---|
| $SC_9CH_3$ | 21 | 600 | 15 | 71 | 0.12 |
| $SC_{11}CH_3$ | 19 | 600 | 15 | 79 | 0.25 |
| $SC_{13}CH_3$ | 20 | 600 | 15 | 75 | 0.22 |
| $SC_{15}CH_3$ | 19 | 600 | 15 | 79 | 0.16 |
| $SC_{17}CH_3$ | 17 | 600 | 15 | 88 | 0.15 |
| total | 96 | 3000 | 75 | 78[a] | 0.18[a] |

[a]These numbers are average values.

Figure 6:
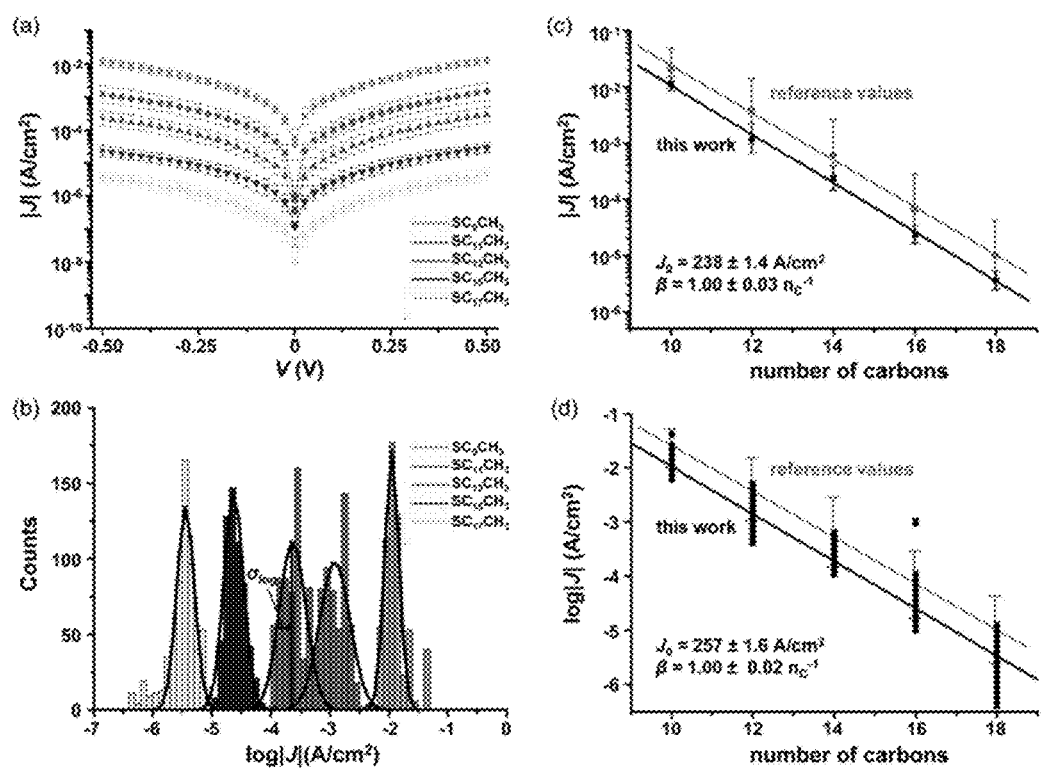
FIG. 6 shows graphs of data obtained from using the electric contact according to an embodiment of the present invention.

Table 2 summarizes the characteristics of the junctions. We excluded shorts and open circuits and kept the number of working junctions constant so the data for all junctions carry the same weight in our analysis. FIG. 6 shows the averaged J(V) curves over all users for each type of junction, the histograms of log|J| at −0.50 V, and plots of <|J|> versus $n_C$. Fitting the data to the Simmons equation gave values of β of 1.00±0.03 $n_C^{-1}$ and $J_0$ of 2.4×10$^2$ A cm$^{-2}$ (using method 1: fitting the Simmons equation to the Gaussian means of log J by least squares fitting). We note that the value of $J_0$ is not precise because of the long extrapolation. The value of β is very close to the consensus value, and the value of $J_0$ is very close to previously reported values obtained for other types of junctions with $GaO_x$/EGaIn top-electrodes (See Table 3 and below). These results indicate that the dominant mechanism of charge trans-port across our junctions is through-bond tunneling.

One may argue that if the distribution of log|J| deviates from normality, it is more accurate to estimate trend statistics by fitting all values of log|J| by a least-absolute-errors algorithm (using method 2: Fitting the Simmons equation to all values of log J by minimizing the absolute error) and) rather than by fitting Gaussian means of log|J| with a least-squares algorithm (method 1) since the former method does not assume any type of distribution while the latter method does. FIG. 6d shows the plot of all values of log|J| at −0.50 V versus $n_C$ with a fit to the Simmons equation using method 2. The values of β and $J_0$ were found to be 1.00±0.02 $n_C^{-1}$ and 257±1.6 A cm$^{-2}$, respectively. Considering the small differences in the values of β and $J_0$ obtained by methods 1 and 2, we believe that the assumption that our data follow a normal distribution introduces a negligibly small error in the analysis of our data.

5. Precision of the Data

The striking difference of the current fabrication method with respect to other methods is that the values of log-standard deviation (σ log) are very small and fall in the range of 0.12 to 0.25 with an average of 0.18±0.05; these values are one of the lowest in general (see Table 3). Thus our method generates J(V) data with very high precision.

TABLE 3

Comparison of $\sigma_{log}$, β, and yield of different tunneling junctions with SAMs.

| Type of junction | Technique | N | $\sigma_{log}$ | β [$n_C^{-1}$] | yield [%] | $N_{max}^{k)}$ | Refs. |
|---|---|---|---|---|---|---|---|
| Ag-SAM//SAM-Hg | Hg-drop | 1-5 | =1.0-1.5[c] | 0.80 | NA | 13 | [32] |
| Hg-SAM//Hg | Hg-drop | 5-10 | =0.11-0.6[c] | 1.06 ± 0.04 | NA | 10 | [38] |
| Hg-SAM//SAM-Hg | Hg-drop | 5-10 | =0.11-0.43[c] | 1.02 ± 0.07 | NA | 10 | [38] |
| Si-SAM//Hg | Hg-drop | >7 | =0.37-0.70[c] | 0.76 ± 0.09 | NA | NA | [88, 97] |
| Al/Al$_2$O$_3$-SAM//Hg | Hg-drop | 12-18 | 0.25-0.75 | 1.34 ± 0.004[h] | 25-75 | 18 | [41] |
| M-SAM//M[a] | CP AFM | 5-10 | =0.28-1.0[c,d] | 1.1 | NA | 10 | [42] |
| Au-SAM//Au | STM break junction | 3000 | 0.02-10[d] | 0.94-0.96 | 10-40 | NA | [94] |
| Ag-SAM//Ag | STM break junction | 7000 | =0.16-0.32[f] | 0.98 ± 0.05[i] | NA | NA | [95] |
| Au-SAM//Au | nanoskiving | >10 | =0.05-0.28[c] | 0.94 | 36-67 | 32 | [85] |
| Si-SAM//Au | PALO[b] | >10 | =0.05-0.26[c] | NA | NA | NA | [92] |
| Si-SAM//Au | flip chip lamination | >30 | =0.06-0.1[c,g] | NA | 90 | NA | [89] |

TABLE 3-continued

Comparison of $\sigma_{log}$, β, and yield of different tunneling junctions with SAMs.

| Type of junction | Technique | N | $\sigma_{log}$ | β [$n_C^{-1}$] | yield [%] | $N_{max}^{k)}$ | Refs. |
|---|---|---|---|---|---|---|---|
| Au-SAM//Au | crossed-wires | NA | =0.22$^{c,e)}$ | NA | NA | NA | [90] |
| Au-SAM//polymer/Au | PEDOT:PSS/micropore | >17 | =0.11-0.15$^{c)}$ | 0.71 ± 0.06 | >95 | 100 | [93] |
| Au-SAM//polymer/Au | PEDOT:PSS/micropore | 74 | =0.23$^{c)}$ | 1.33 ± 0.05 | 58 | 74 | [39] |
| Au-SAM//Au | SiO$_2$ micropole | 33-63 | 0.23-0.527 | 1.04-1.08 | 1.2-1.75 | NA | [26] |
| Au-SAM//Au | Si$_3$N$_4$ nanopore | =160 | =0.27-0.32$^{c)}$ | 1.07 ± 0.02 | 7.1 | NA | [14] |
| Au-SAM//Au | wedging transfer | 200-340 | 0.57-1.13 | 0.73 ± 0.06 | 38-50 | NA | [86] |
| Au-SAM//graphene/Au | graphene/micropore | 258 | =0.27-0.67$^{c)}$ | 1.06 ± 0.14 | 90 | 2000 | [87] |
| graphene-SAM//graphene | graphene//micropore | >50 | =0.17-0.35$^{c)}$ | 0.54 ± 0.01 | >80 | NA | [91] |
| Ag-SAM//GaO$_x$/EGaIn | cone-shaped tip | 376-3892 | 0.23-1.1 | 1.04 ± 0.06$^{j)}$ | 82-100 | NA | [40] |
| Ag-SAM//GaO$_x$/EGaIn | Flattened cone-shaped tip | 360-480 | 0.3-0.7 | 0.92 ± 0.02 | =90% | NA | [46] |
| Ag-SAM//GaO$_x$/EGaIn | cross-bars | 400-756 | 0.21-0.85 | 0.98 ± 0.2 | 70-85 | NA | [16] |
| Ag-SAM//GaO$_x$/EGaIn | through-hole | 600 | 0.12-0.25 | 1.00 ± 0.03 | 78 | 2500 | this work |

$^{a)}$A metal-coated (Au, Ag, or Pt) AFM tip was contacted with a SAM on a Au-, Ag-, or Pt-coated Si substrate;
$^{b)}$Polymer-assisted lift-off method;
$^{c)}$Roughly estimated from the J(V) curves in the corresponding references;
$^{d)}$The log standard deviations of the resistance instead of current density were measured;
$^{e)}$The standard deviations of the conductance instead of current density were reported;
$^{f)}$The log standard deviations of the conductance instead of current density were reported;
$^{g)}$The standard deviations of the current at 1 V instead of current density were reported;
$^{h)}$This value was reported for C8-C12 junctions. The value was reported to be 0.77 ± 0.005 for the junctions of C12-C16;
$^{i)}$The β value was measured to be 0.93 ± 0.05 $n_C^{-1}$ when the Au tip was used to measure the junctions of SAMS on Au substrates;
$^{j)}$This value was obtained by measuring the SAMs of n-alkanethiolate with even number of carbons in the molecules. The value of β was found to be 1.19 ± 0.08 $n_C^{-1}$ for SAMs of n-alkanethiolate with odd number of carbons in the molecules;
$^{k)}$The maximum number of continuous scans without shorting or becoming open circuit for a single junction. These numbers are either shown or indicated in the papers.

Figure 7:
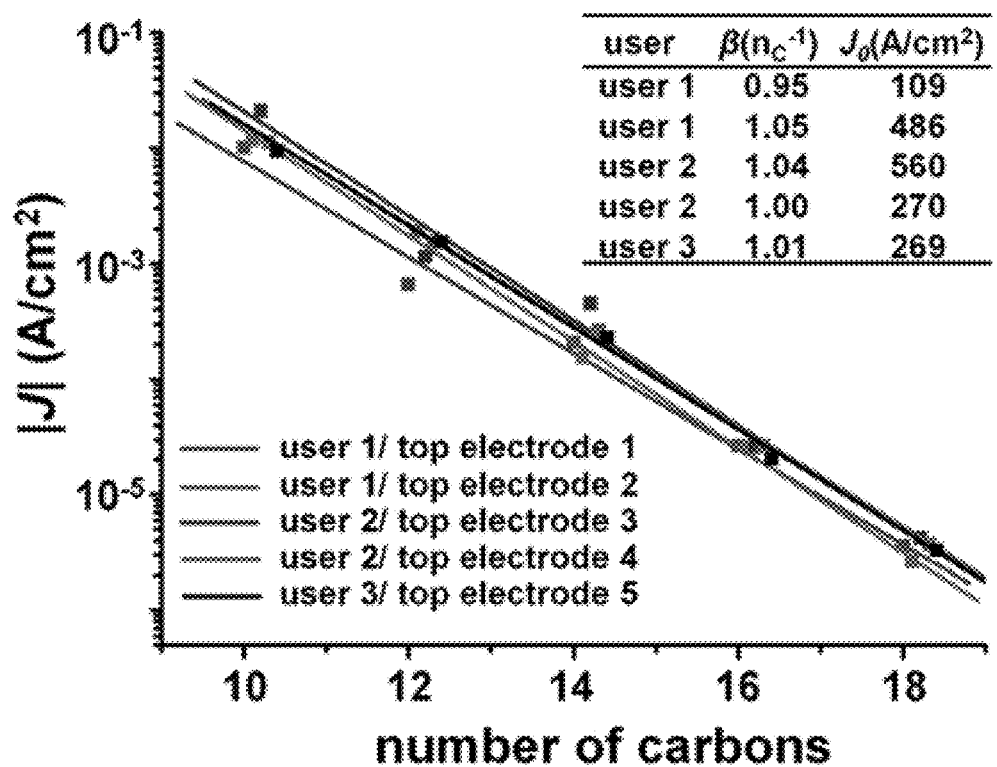
FIG. 7 shows a graph of data obtained from using the electric contact according to an embodiment of the present invention.

To determine reproducibility between different top-electrodes and different investigators we performed two experiments: three investigators measured the electrical characteristics of the junctions using i) five different top-electrodes each operated by one of the three investigators, or ii) one top-electrode operated by all three investigators. FIG. 7 shows the corresponding five plots of log|J| versus $n_C^{-1}$ determined by three different users using five different top-electrodes. Each plot was measured by one user and top-electrode combination as indicated in the Figure. FIGS. 13 to 17 show the corresponding histograms of log(|J|) determined at −0.50 V for all Ag$^{TS}$—SC$_n$//GaO$_x$/EGaIn junctions for each user and top-electrode combination. The values of obtained from these plots were all in the range of 0.95-1.05 $n_C^{-1}$ with values of $J_0$ ranging from 109-560 A cm$^2$ (see inset of FIG. 7). Note that we give a range of values rather than standard deviations because the number of J(V)-curves is per user lower than the total number of data; these numbers are not precise but reasonably replicable because they all are in the range of previously reported values of 0.2-2×10$^3$ A cm$^{-2}$ (Table 1). FIGS. 13 to 17 show the histograms of log|J| measured at −0.50 V for junctions with SAMs of SC$_9$CH$_3$, SC$_{11}$CH$_3$, SC$_{13}$CH$_3$, SC$_{15}$CH$_3$, and SC$_{17}$CH$_3$, respectively. In our measurements, three junctions with 40 J(V) traces for each junction were collected for each type of SAMs by using the same top-electrode conducted by three different users. This procedure was repeated for five times with five different top-electrodes. By fitting the histograms of log|J| at −0.50 V to Gaussians, we determined the average log|J| values and log-standard deviations following previously reported procedures.

To investigate if the data depend on the users, we also examined the histograms of the values of log|J| at −0.50 V for junctions with SAMs of SC$_{17}$CH$_3$ obtained by three different users using the same top-electrode. FIG. 7 shows that the data are independent of the user who conducted the measurement. These results indicate that the values of log|J| and β are narrowly distributed and independent of the user or top-electrode: the data produced by our technique is precise with respect to different operators and top-electrodes.

6. Replicability of the Data

Figure 8:
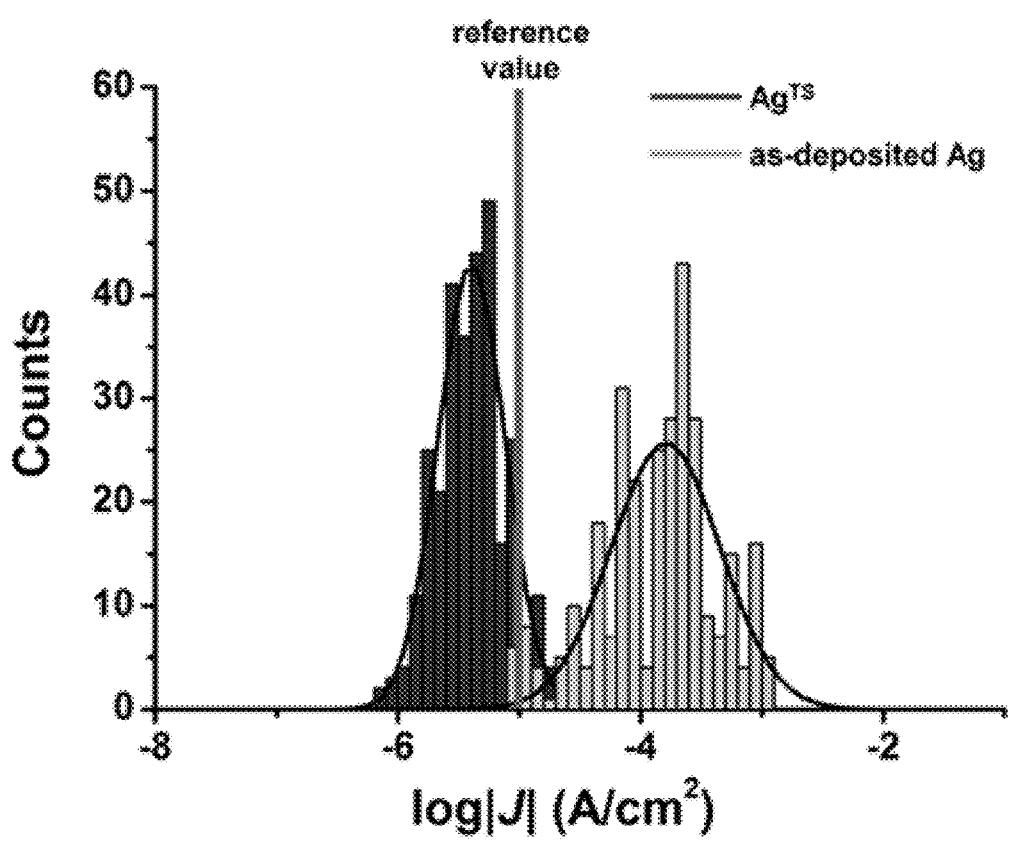
FIG. 8 shows a histogram of data obtained from using the electric contact according to an embodiment of the present invention.
Figure 12:
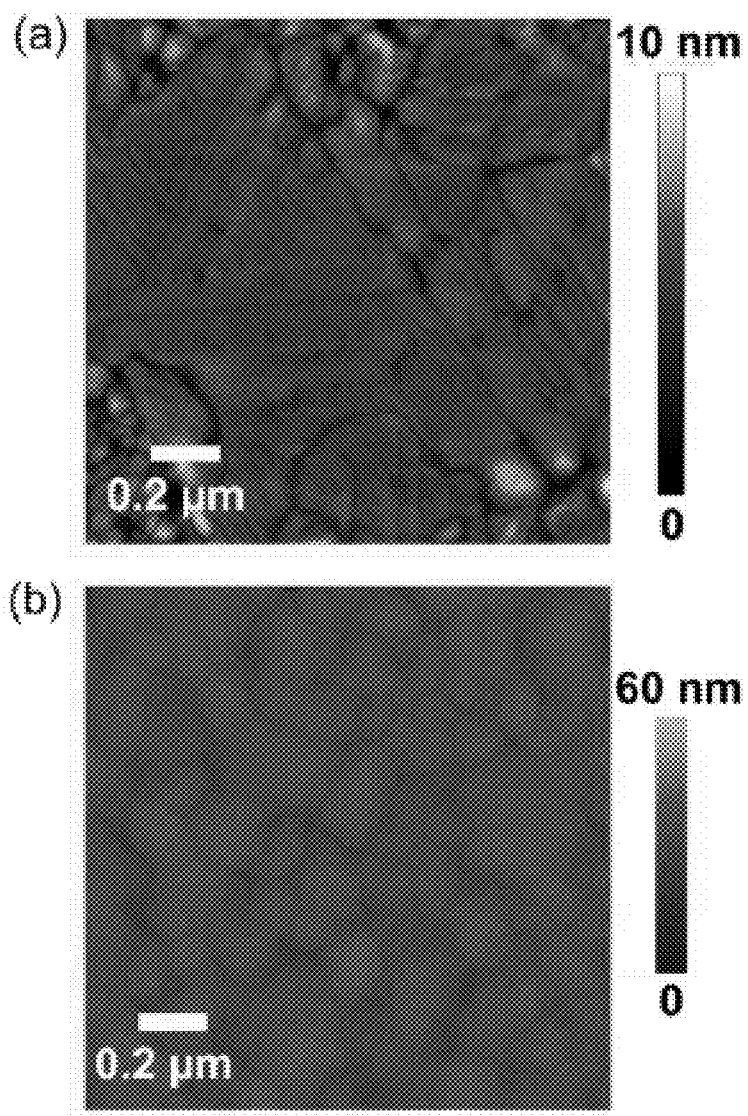
FIG. 12 shows AFM images of a template-stripped Ag surface and an as-deposited Ag surface.
Figure 13:
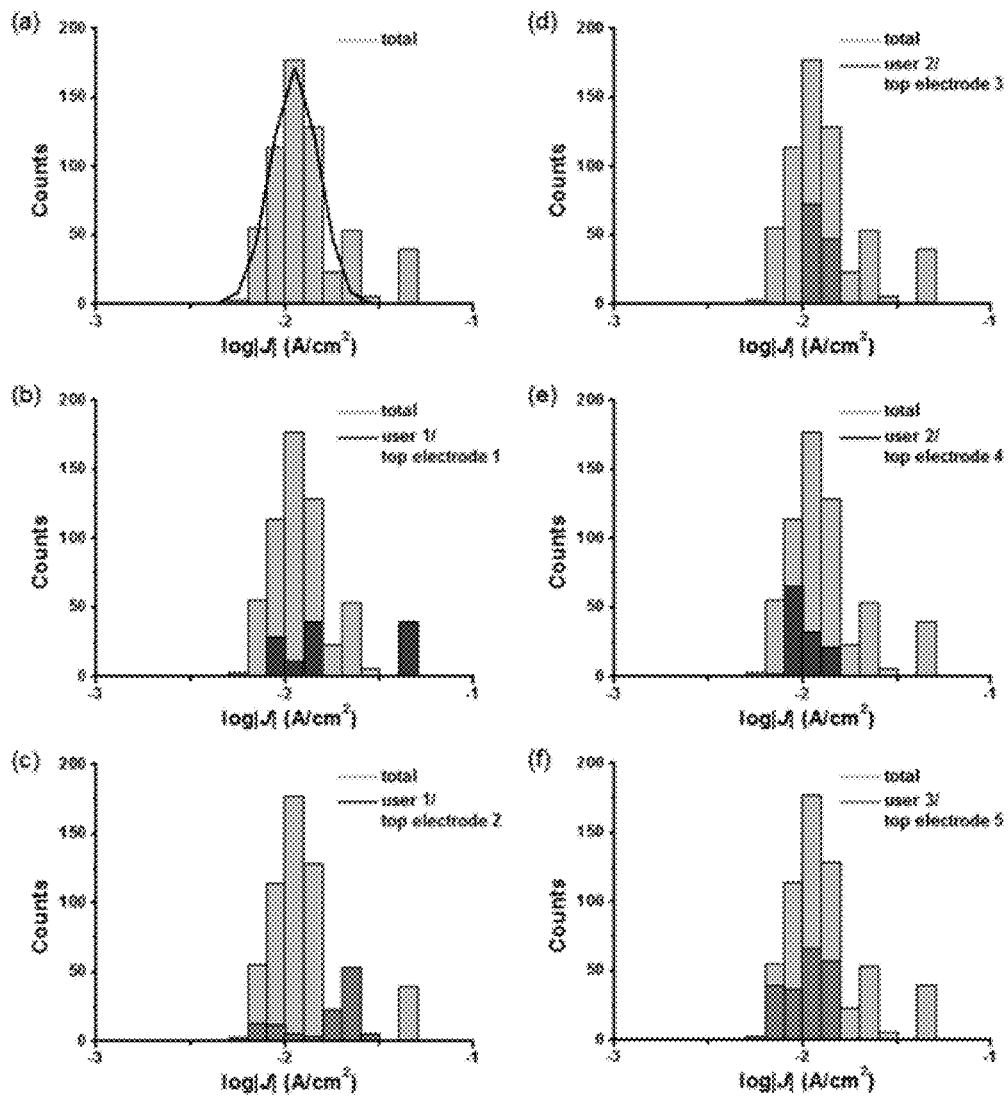
FIGS. 13 to 17 show histograms of data obtained from using the electric contact according to an embodiment of the present invention.
Figure 14:
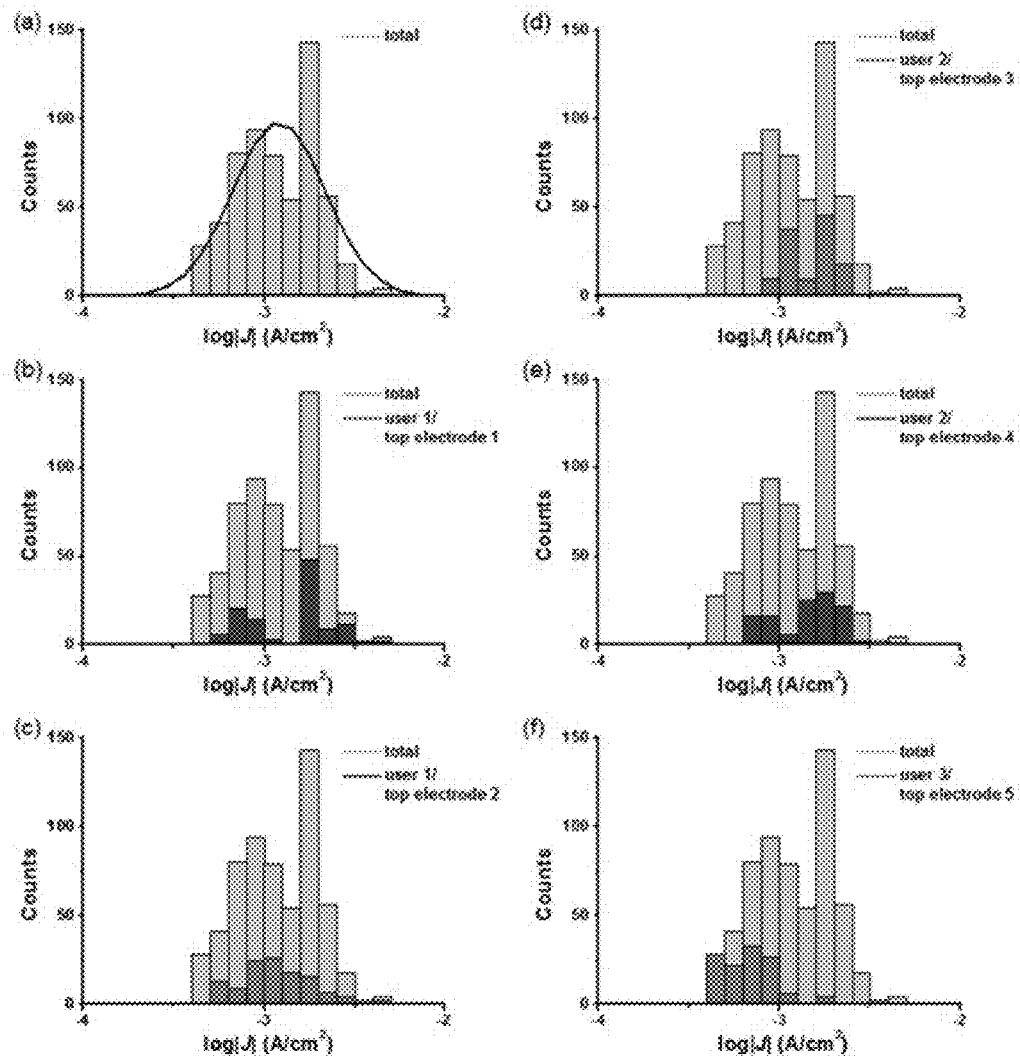
Figure 15:
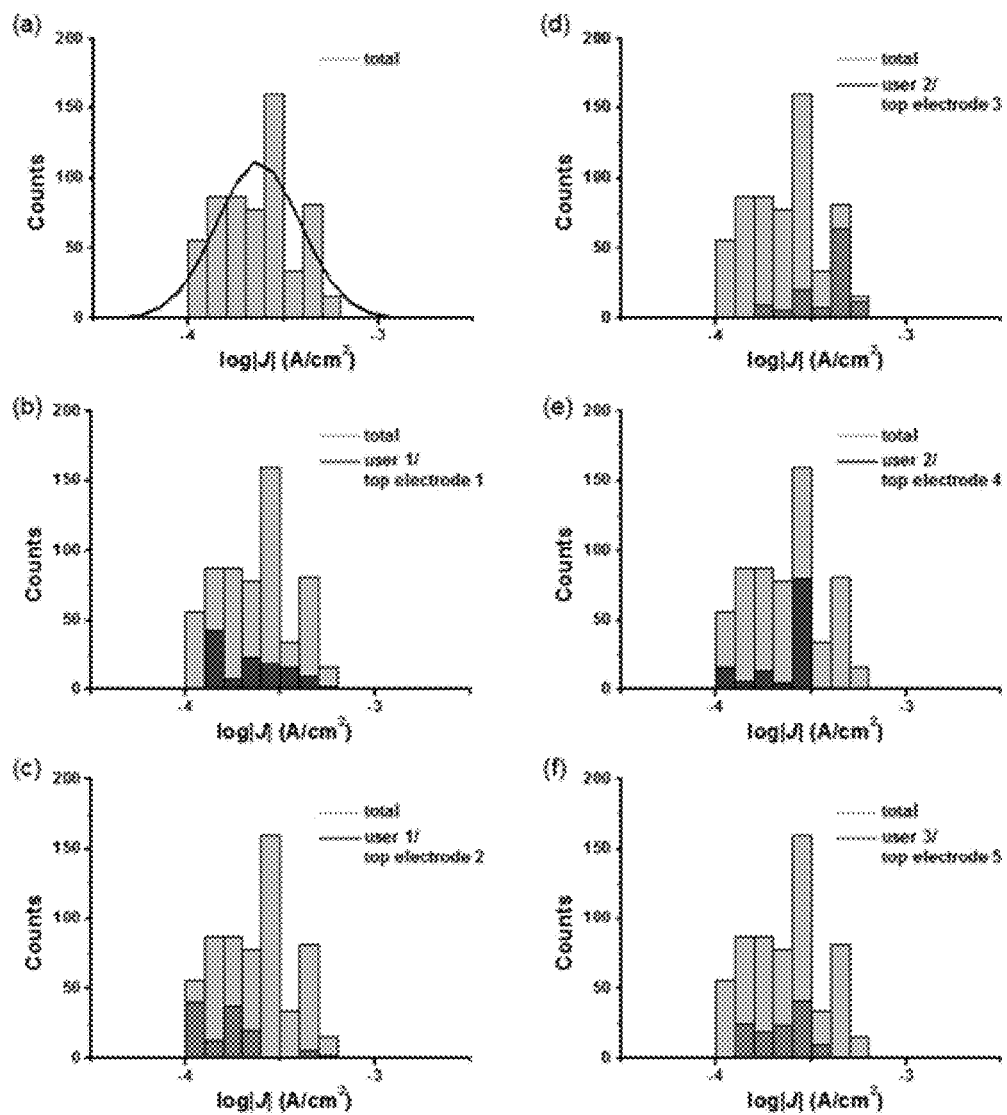
Figure 16:
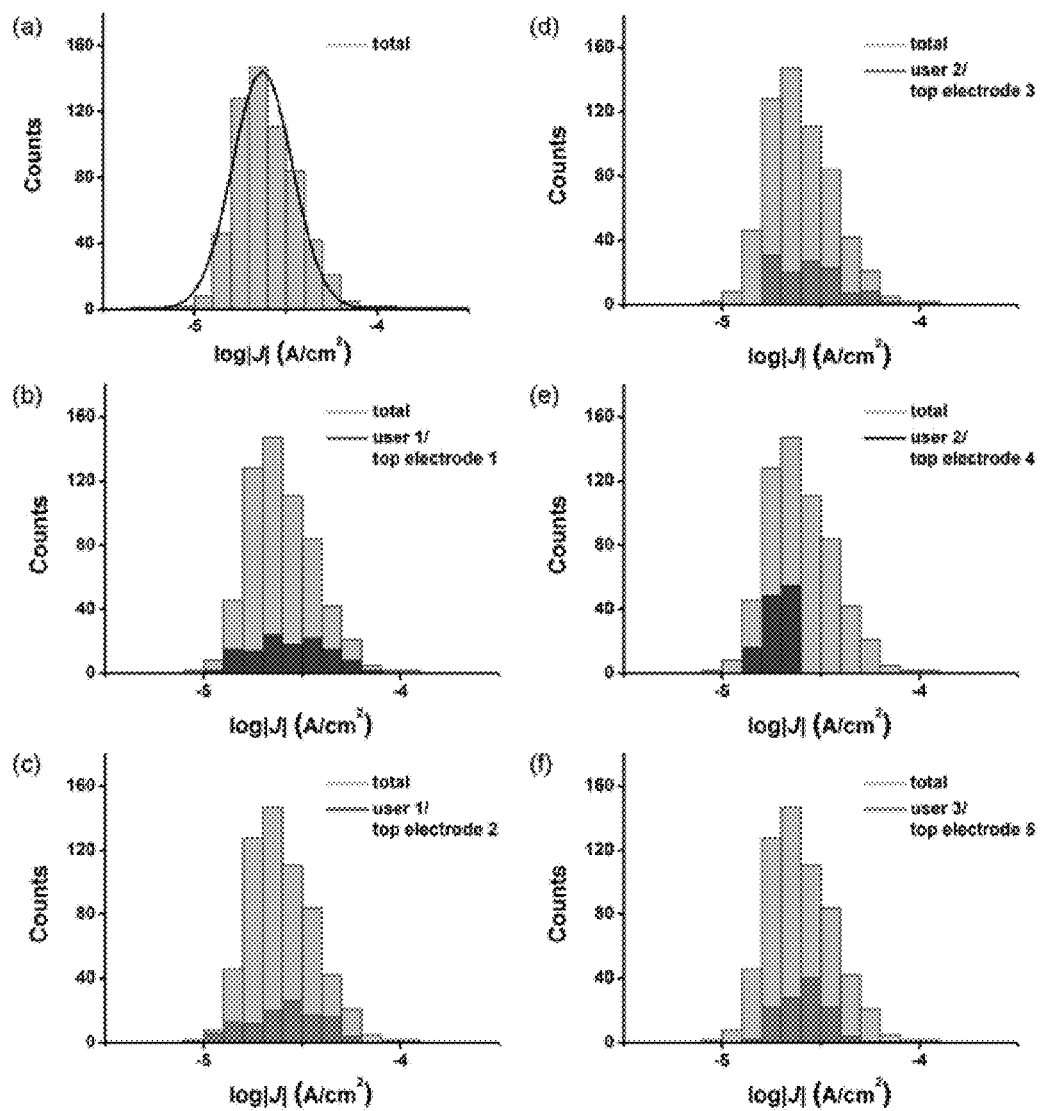
Figure 17:
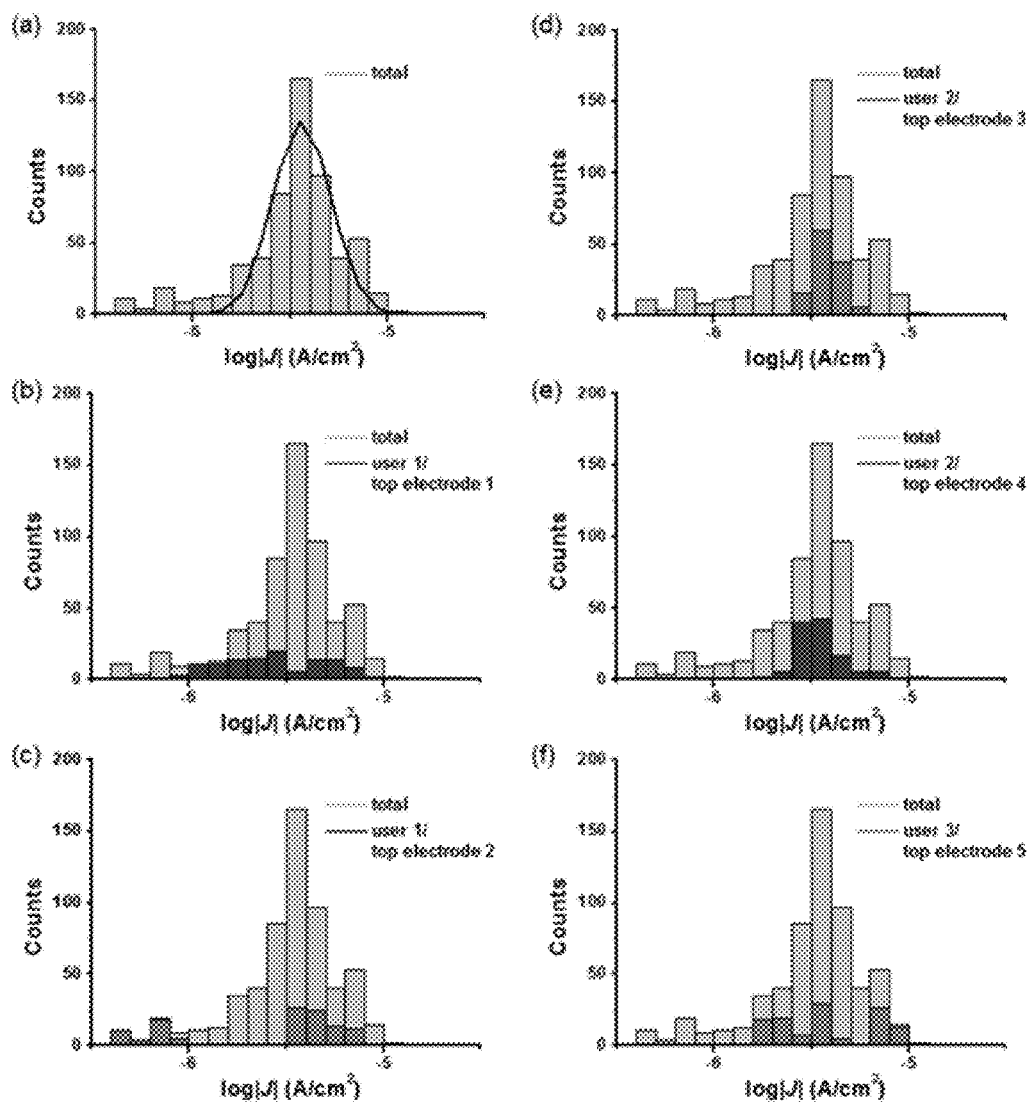

As mentioned earlier that junctions with TS bottom-electrodes result in junctions with higher yields in non-shorting junctions with smaller log-standard deviations than those junctions with direct metal deposited bottom-electrodes, but the authors did not discuss whether the topography of the bottom-electrode is important in the replicability of the data. To determine if the topography of the bottom-electrode is an important source for lowering the replicability, we formed SAMs of SC$_{17}$CH$_3$ (using the same batch of the thiol precursor) on as-deposited Ag substrates, which had a rms roughness of 3.3 nm and small grains of <3×10$^{-2}$ μm$^2$, and on TS surfaces, which had a rms roughness of 0.9 nm and large grains of 0.05-0.9 μm$^2$ in agreement with previously reported data (see FIG. 12 for AFM images). Subsequently, we formed junctions using one top-electrode operated by one investigator. FIG. 8 shows that the values of J increased nearly two orders of magnitude and the σ log increased from 0.26 to 0.58 as we changed the bottom-electrode from Ag$^{TS}$ to as-deposited Ag. This change in the topography of the bottom-electrode resulted in large decrease in the precision and replicability of the J(V) data. The exact rms values and grain sizes of the bottom-electrodes depends on many factors including deposition rate, base-pressure of the vacuum chamber, pre-treatment of the target surface, and so forth. Thus, small variations in the topography of the bottom-electrode can be a source of data broadening and may cause shoulders or even new peaks in histograms of J. To maximize the precision and replicability of the J(V) data generated by our method, we record AFM images for every new batch of electrodes and only use surfaces similar to that shown in FIG. 12a before we start experiments. FIG. 12(a) shows an AFM image of a template-stripped Ag surface, while FIG. 12(b) shows an AFM image of a as-deposited (thermal) Ag surface. The rms roughness of the template-stripped and the as-deposited Ag surfaces were determined to be 0.9 and 3.3 nm (over an area of 1×1 μm) respectively.

Figure 9:
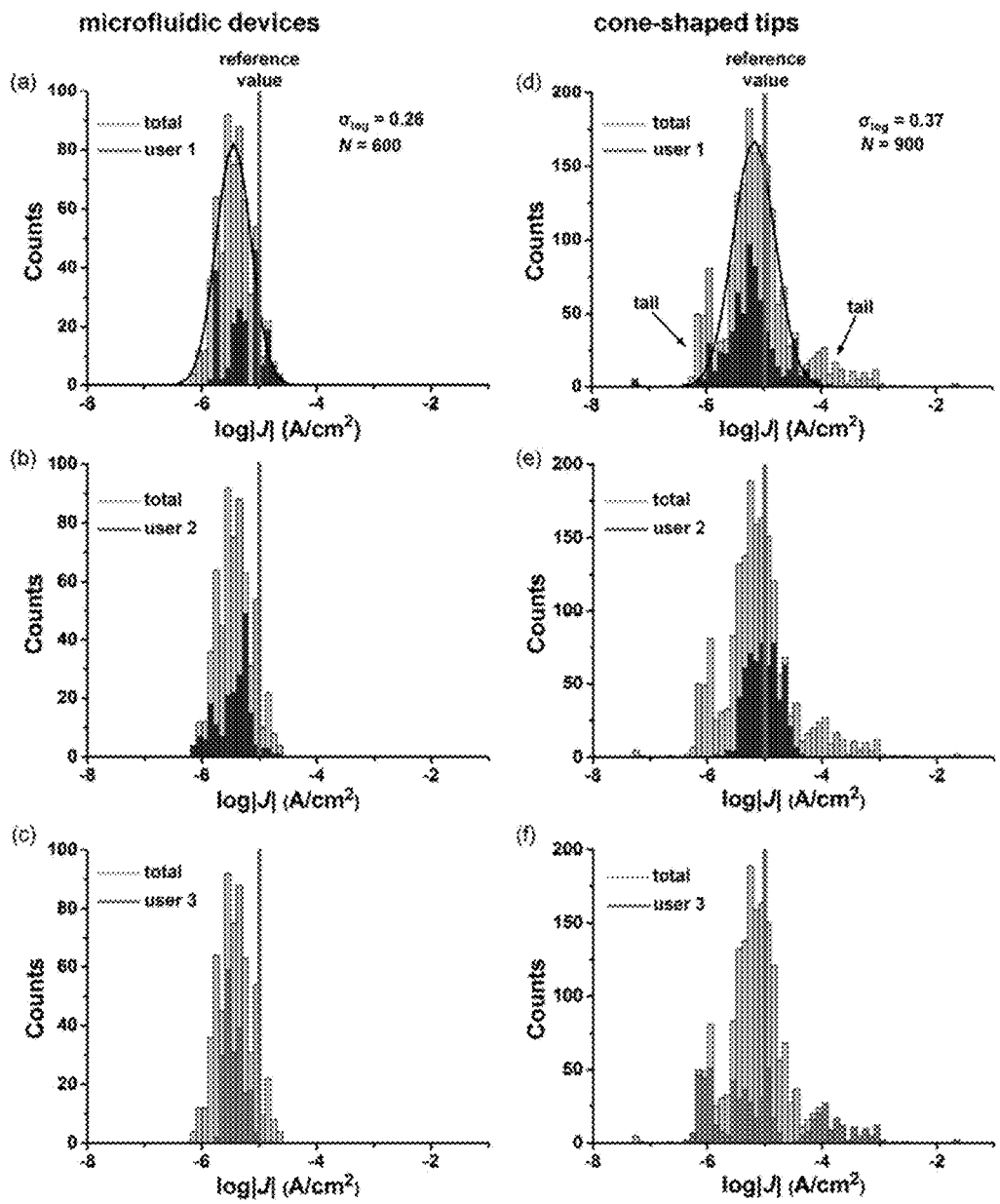
FIG. 9 shows histograms of data obtained from using the electric contact according to an embodiment of the present invention.

To show that stabilization of the GaOx/EGaIn in the through-hole in PDMS contributes to the precision of the data, we measured the J(V) characteristics of junctions with SAMs of $SC_7CH_3$ with top-electrodes of GaOx/EGaIn stabilized in PDMS (FIG. 9a) or with cone-shaped tips of GaO/EGaIn operated by three investigators (FIG. 9b). FIG. 9 shows that both data sets have their log-mean value of J close to the reference value. The widths of both distributions are comparable, but shoulders on both sides of the main peak are visible which mainly originated from one of the three operators for junctions with cone-shaped tips of $GaO_x$/EGaIn. Thus, in this experiment user-to-user correlation was significant. These results are similar to those reported earlier who collected large values of $N_J$ of up to a few thousand by multiple investigators and reported broad distributions that contained multiple peaks. Junctions prepared with cone-shaped tips of $GaO_x$/EGaIn vary in details of the formation of the tip and the formation of the junctions that differ from user-to-user. The stabilization of the top-electrode in microfluidic device minimizes the user-to-user variations in the formation of the top-electrodes, the geometric area of the junctions, and the potential error associated with vibrations and drift of the cone-shaped tip of GaOx/EGaIn mounted on a micro-manipulator as top-electrodes resulting in precise data.

7. Stability of the Devices

Figure 10:
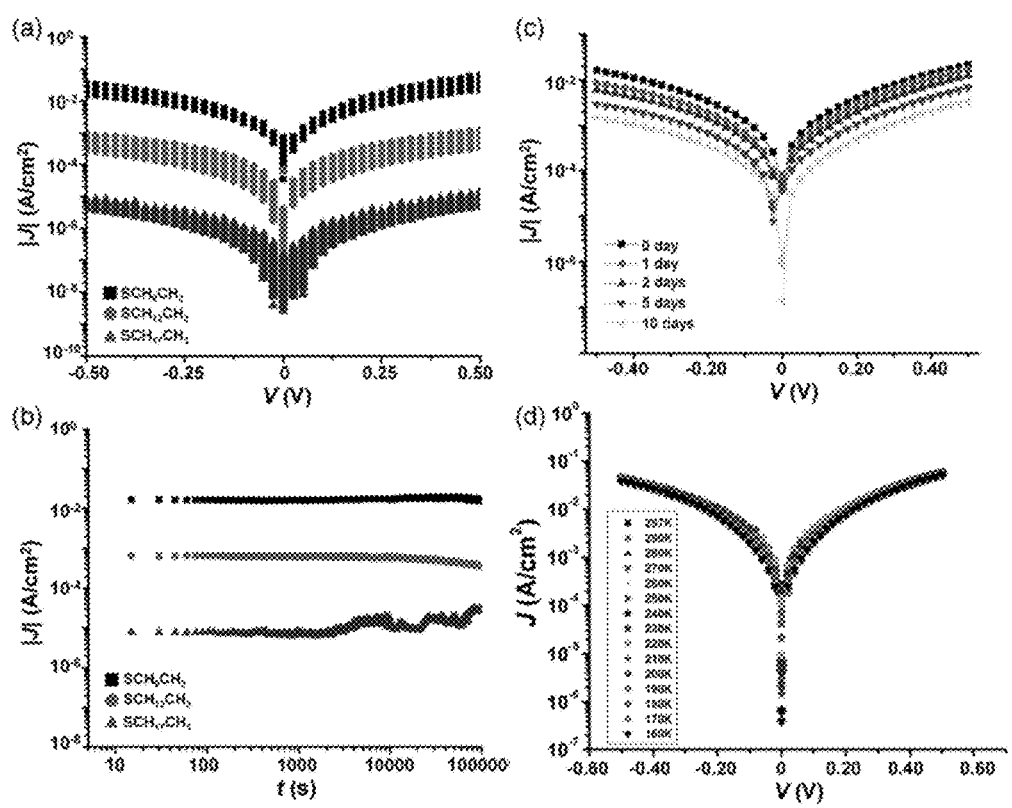
FIG. 10 shows graphs showing the stability of the junctions using the electric contact according to an embodiment of the present invention.
Figure 19:
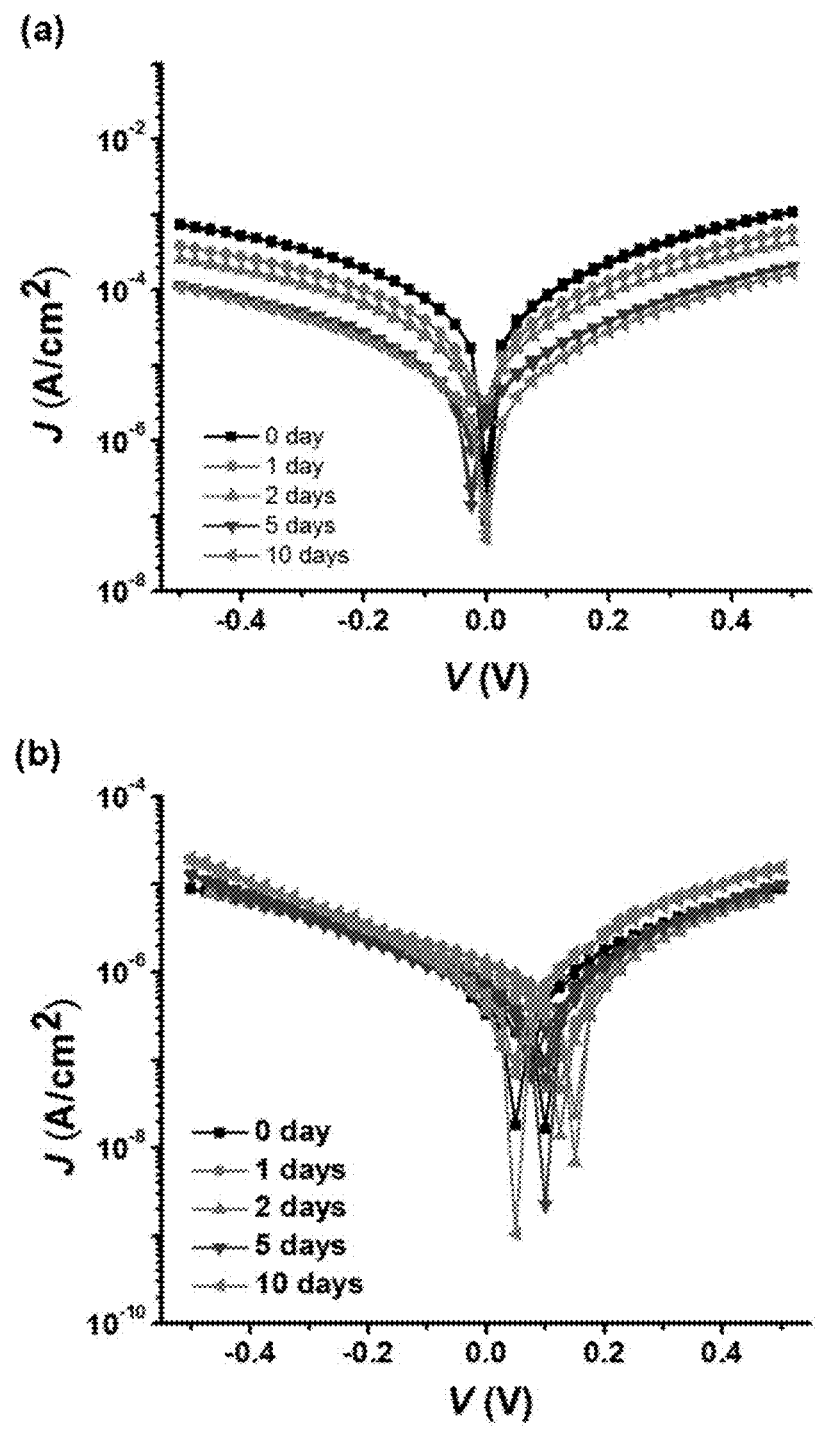
FIG. 19 show J(V) curves of junctions with SAMs of (a) $SC_{13}CH_3$, or (b) $SC_{17}CH_3$ right after the devices according to embodiments of the present invention were prepared and after the devices were left for several days.

To ensure our test-bed can be used as a reliable platform for studying charge transport across SAMs, it is crucial to know the electrical stability and the lifetime of these devices. We tested the electrical stabilities of the devices incorporating SAMs of $SC_9CH_3$, $SC_{13}CH_3$ and $SC_{17}CH_3$ against continuous cycling of voltage (2500 cycles of 0 V→0.50 V→−0.50 V→0 V), bias stress (by applying a constant bias of −0.50 V for $10^5$ seconds), and aging (ambient conditions at room temperature) over a period of time of ten days. FIG. 10a shows that these devices are electrically stable and did not short during voltage cycling. FIG. 19 shows the values of J (at −0.50 V) as a function of cycle number. The value of J for the junction with $SC_9CH_3$ was more stable than those junctions with SAMs of $SC_{13}CH_3$ (noisy around cycle number 975-985) and $SC_{17}CH_3$ (noisy for cycle number>1500). FIG. 10b shows the retention characteristics of the devices. The junctions with SAMs of $SC_9CH_3$ and $SC_{13}CH_3$ were more stable than the junction with $SC_{17}CH_3$ which became noisy after $3.0 \times 10^3$ s. One possible reason for the difference in the electrical stability between the devices is that SAMs with long alkyl chains are more crystalline and therefore contain more defects from, for example, phase domains boundaries than the short liquid-like SAMs. FIG. 10c shows the J(V) curves of the device with SAMs of $SC_9CH_3$ determined at t=0, 1, 2, 5, and 10 days. Over this period of time, the values of J decreased by approximately a factor of seven. A similar behavior was observed for devices with $SC_{13}CH_3$, and $SC_{17}CH_3$ SAMs (see FIG. 20). The reason for the change in current densities is unclear, but it may involve oxidation of the metal-thiolate bonds or the formation of silver sulfides.

Measurements of J(V) as a function of temperature T(K) are important to establish the mechanism of charge transport across tunnel junctions. To test the stability of the devices against changes in temperature, we studied the electrical characteristics of the devices over a range of values of T of 160-297 K. These measurements were performed in a probe station at a pressure of $1 \times 10^{-5}$ bar. In agreement with previous observations, both the change of pressure from ambient to vacuum and solidification of the bulk EGaIn at T=220-240 K did not result in shorts, open circuits, or changed the electrical char-acteristics of the devices notably in any other way. FIG. 10d shows that the J(V) curves of devices with SAMs $SC_9CH_3$ are (almost) independent of temperature as expected when tun-neling is the dominant mechanism of charge transport. The devices shorted at the temperature lower than 160 K likely due to the differences in the thermal expansion coefficients of the different components in the devices ($3 \times 10^{-4}$ K$^{-1}$ for PDMS, $0.08 \times 10^{-4}$ K$^{-1}$ for glass, $0.042 \times 10^{-4}$ K$^{-1}$ for $Ga_2O_3$, $0.18 \times 10^{-4}$ K$^{-1}$ for EGaIn).

The following is a description of the electrical measurements:

(a) Electrical Measurements Using $GaO_x$/EGaIn Cone-shaped Tips

The experiments involving junctions with cone-shaped tips of $GaO_x$/EGaIn were conducted using a home-built set-up. The set-up contained a micromanipulator (Leica) equipped with a 10-μl glass syringe (Hamilton, 1701 RNR) with a metallic needle (Hamilton, conical shape 26s) and a tungsten probe (Signatone, SE-T) connected to a Keithley 6430 source meter. The formation of tips and the junctions have been described previously. Briefly, we filled the syringe with $GaO_x$/EGaIn and pushed a drop of $GaO_x$/EGaIn out of the syringe and brought the $GaO_x$/EGaIn droplet hanging from the needle in contact with a sacrificial substrate. Once the $GaO_x$/EGaIn droplet stuck on the substrate, we slowly pulled the syringe needle from the droplet using the micro-manipulator. A conical shaped tip of $GaO_x$/EGaIn formed suspended from the syringe needle once it disconnected from the $GaO_x$/EGaIn at the surface.

(b) Proposed Reference Values for EGaIn-based Techniques

Figure 18:
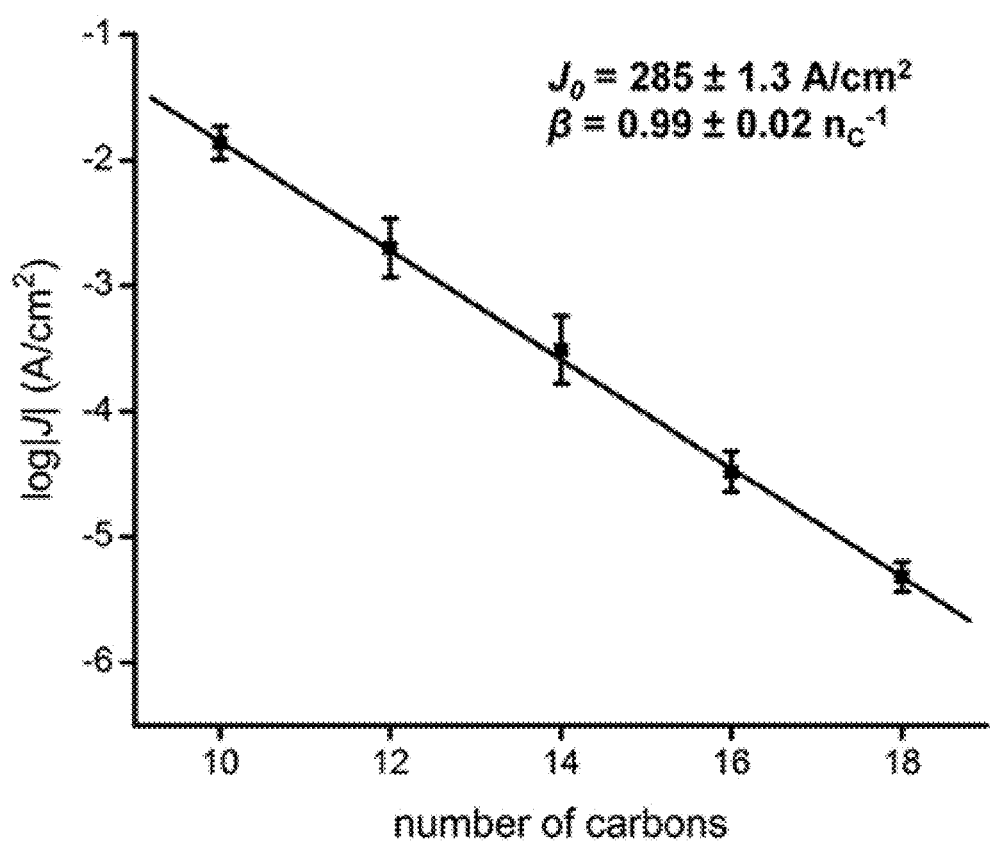
FIG. 18 show Plots of the average values of log|J| measured at −0.50 V using different EGaIn-based techniques for n-alkanethiolate self-assembled monolayer (SAMs)— fthe solid line represent the fit to the Simmons equation.

We determined the reference values of β and $J_0$ by least squares fitting the average <log|J|> (the values are shown in Table S1 below) using the Simmons equation (see FIG. 18).

TABLE S1

Summary of GC-MS area percent report of $SC_nCH_3$ (n = 10, 12, 14, 16, 18).

| Compound | Peak | Retention time (minutes) | Area | Total (%) |
|---|---|---|---|---|
| $C_{10}SH$ | 1 | 11.95 | $4.3 \times 10^8$ | 98.2 |
|  | 2 | 21.92 | $7.8 \times 10^6$ | 1.8 |
| $C_{12}SH$ | 1 | 14.75 | $1.6 \times 10^8$ | 100.0 |
| $C_{14}SH$ | 1 | 16.77 | $3.2 \times 10^8$ | 100.0 |
| $C_{16}SH$ | 1 | 18.24 | $1.5 \times 10^7$ | 100.0 |
| $C_{18}SH$ | 1 | 19.45 | $9.3 \times 10^7$ | 100.0 |

Figure 20:
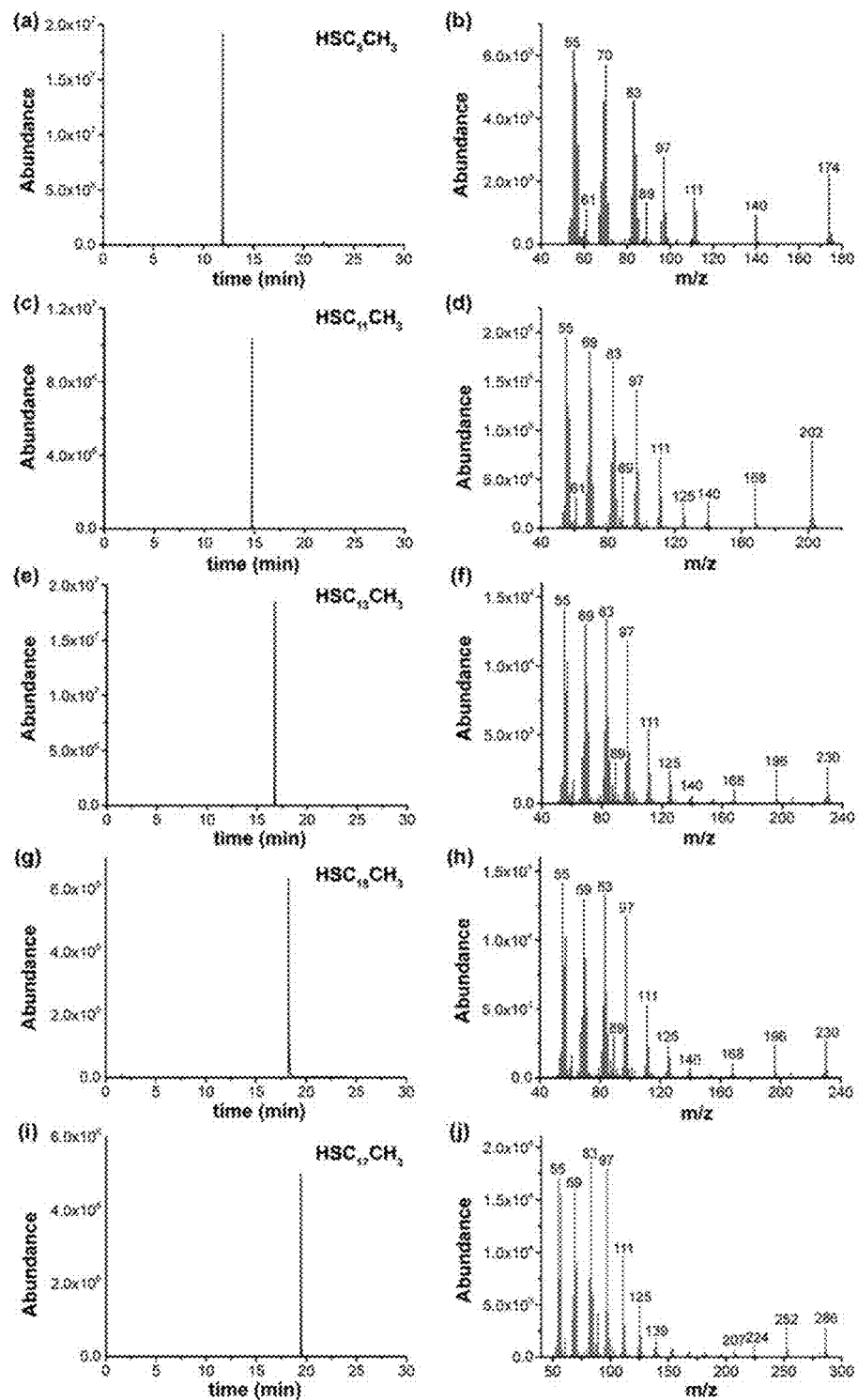
FIG. 20 show the GC-MS and the corresponding MS spectra of $HSC_{n-1}CH_3$ with n=10 (a and b), 12 (c and d), 14 (e and f), 16 (g and h), and 18 (i and j).

It is well-known that thiols can decompose to form disulfides and sulfonates in ambient conditions. All the as-received n-alkanethiols (Sigma-Aldrich) were recrystallized from ethanol (AR grade) under atmosphere of $N_2$ at −20° C. followed by quick filtration prior to use. In case of insoluble impurities, the ethanolic thiol solutions were filtered before recrystallization. FIG. 20 and Table S1 show the GC-MS spectra and the corresponding analytical results, respectively of the n-alkanethiolates after the purification. These results reveal that after the purification, the concentration of $HSC_9CH_3$ was more than 98.7% with trace amount of disulfides, while no impurities were found in $HSC_{11}CH_3$, $HSC_{13}CH_3$, $HSC_{15}CH_3$ and $HSC_{17}CH_3$.

8. Comparison to Other Test-Beds

To judge the performance of our method against previously reported test-beds, we compared i) yields in working junctions, ii) log-standard deviations as an indicator of reproducibility or precision, iii) values of β as an indicator of the replicability or quality of the junctions (lower or higher values than the con sensus value of 0.9-1.1 $n_C^{-1}$ are likely caused by artifacts), and iv) the stability against voltage cycling (crudely judged from the number of scans), and v) the ability to generate statistically large numbers of data. Our fabrication technique give devices with i) yield larger than 75%, ii) values of σ log smaller than 0.3, iii) β of 1.00±0.03 $n_C^{-1}$, iv) good electrical stability (2500 times of voltage cycling), and v) produces statistically large numbers of data (N>600). In Table 3 we highlighted techniques that have comparable or better characteristics than ours in bold. Although these criteria are arbitrary chosen and this comparison gives a crude impression at best how different test-beds perform relative to ours, this effort hopefully serves as a starting point to judge methods not only by yields in non-shorting junctions, or the value of β, but also by more criteria including stability and more importantly reproducibility and replicability.

Table 3 is not comprehensive, but we included data obtained by large-area SAM-based junctions that contain large numbers of molecules, and techniques based on scanning probes that contain small numbers of molecules or even single molecules. In typical scanning tunneling microscope (STM) measurements, the air or vacuum gap between the tip and the molecules complicates evaluating the true conductance of the molecules. The so-called STM break junction technique forms junctions by capturing the molecules between the STM tip and the bottom-electrode in situ from solution. Although this technique produces large numbers of data, little information is available regarding the supramolecular structure of the junctions. Direct deposition of the top-electrodes on SAMs resulted in low yields of non-shorting junctions and is prone to metal filament formation, and other types of defects. Using a conductive layer (polymer or graphene based materials) between the SAM and the top-electrode protects the SAM during metal deposition and increased the yields. Other techniques have avoided metal deposition by using liquid-metal top-electrodes (Hg or $GaO_x$/EGaIn) which deform and conform to, rather than penetrate, the SAM once brought into contact with the SAM. Others have deposited solid electrodes from solution or used bending wires to form junctions.

Among the methods that generate values of β that are close to 1.0 $n_C^{-1}$, our method has amongst the smallest σ log values (0.12-0.25). Nanoskiving also generates comparably small σ log values (≈0.05-0.28) with β 0.94 $n_C^{-1}$ but with low numbers of data. Junctions with PDOT:PSS protection layers are generated in very high yields with small errors and good stabilities, but with very low values of β. Junctions with graphene as protection layer perform also well and produce large numbers of data in high yields with β close to 1.0 $n_C^{-1}$, but with a larger error than our method. For most fabrication methods, the stability of the junctions against voltage cycling has not been reported, but our method compares well in stability to that of the rigorously tested junctions with graphene protection layers. Thus, we conclude that our fabrication method generates junctions with high reproducibility, replicability, good electrical stability, and generates statistically large numbers of data in good yields.

CONCLUSION

Here we report a new technique to from electrical top-contacts to SAMs that relies on a top-electrode of a non-Newtonian liquid metal alloy stabilized in a micro-scale through-hole in PDMS. This top-electrode can be directly placed onto the SAMs, removed from the SAMs once the measurements are completed, and used again to form a new junction. Typically 15-25 junctions can be formed with a single top-electrode.

Thus, this method provides the opportunity to investigate the reproducibility of the electrical characteristics of SAM-based junctions as a function of the top-electrodes and users. We found that the electrical characteristics are highly reproducible between different users and top-electrodes: the values of β obtained by three investigators using five different top-electrodes ranged only from 0.95 to 1.05 $n_C^{-1}$ with an average value of 1.00±0.03 $n_C^{-1}$.

Unlike other methods to fabricate SAM-based devices (of the sort shown in FIG. 1), our technique is compatible with template-stripped bottom-electrodes and does not require patterning of the bottom-electrode. This ensures that the electrodes supporting the SAMs are clean and never had been exposed to photoresist (which is often difficult to remove completely) and only briefly exposed to the ambient (few seconds), and do not contain edges at which SAMs cannot pack well. The stabilization of the top-electrode minimizes the user-to-user variation in contacting the SAMs, defines the geometrical area of the junctions. To improve replicability, prior to the SAM formation, we purified the thiols and characterized the template-stripped electrodes by AFM to confirm the quality of the bottom-electrodes. All these factors resulted in very narrow log-normally distributed values of J (σ log=0.12-0.25), i.e., the data generated by our junctions is highly reproducible in terms of precision with high replicability relative to other "EGaIn"-techniques.

This method minimizes the potential error associated with cone-shaped tips of $GaO_x$/EGaIn suspended from a syringe such as vibrations, pressure at which the tip is brought in contact with the SAM, or drift of the tip with respect to the SAM. Therefore it is possible to measure J(V) curves over a range of temperatures of T=160-297 K which confirmed that the dominant mechanism of charge transport is coherent tunneling. We conclude that all "EGaIn"-based techniques produce J(V) data that agree with one another (because the values of $J_0$ vary only a factor of ten which is small relative to the eight to nine orders of magnitude difference across text-beds), but our data are more precise (the distributions of J have small log-standard deviations; Table 1). To date we cannot explain the absolute values of the values of J (or $J_0$) in every detail. It is reported that the GaOx layer is highly conductive and does not affect J significantly, but the effective electrical contact area is smaller than the geometrical contact area and therefore results in an underestimation of the value of $J_0$. We will discuss the role of molecule-electrode contact resistances and defects on the values of $J_0$ elsewhere.

The term "reproducibility" is ill-defined and so is the "quality" of SAM-based junctions. Therefore it is difficult to compare one test-bed to another, but by far most approaches have only focused on the yields in non-shorting junctions and standard deviations. We found that comparing yields and (log) standard deviations only provide marginal information regarding the quality of the junctions. For instance, techniques that produce significantly lower or higher values of β than 1.0 $n_C^{-1}$ with very small standard deviations in high yields are perhaps precise, but are not accurate and likely probe defective junctions. We used the following parameters to evaluate test-beds against each other: i) yields in non-shoring junctions (78%), ii) log-standard deviation (0.12-0.25), iii) value of β (1.00±0.03 $n_C^{-1}$), iv) electrical stability (voltage cycling for 2500 cycles), and v) ability to generate large numbers of data (≥600). We found that our devices exhibit very good overall performance relative to other test-beds and that our junctions are of good quality and pro-duce data that are both precise (Table 3) and replicable (relative to other "EGaIn"-based techniques; Table 1). Although this list is not exhaustive, we believe it serves as a good starting point to evaluate test-beds against each other.

Many fabrication methods use protective layers (to protect the SAMs during the metal deposition process to form the top-contacts) that are deposited by solution based processes, or on the deposition of the electrode from solution. We believe that our method to form electrical contacts to SAMs of n-alkanethiolates can be readily extended to other types of SAMs, monolayers of biomolecules, or other types of materials that may not be compatible with direct deposition methods of metals, or exposure to solvents, to form high quality junctions in good yields with high reproducibility.

The area of the electrical contact may be between 100 to 300 $\mu m^2$, limited by the surface tension of liquid metal. This could be overcome by using different type of liquid metal that has smaller surface tension.

The mechanical stability can be improved by down-sizing the whole devices. The smaller the channels, the more solid the material behaves. Alternatively, any suitable polymers other than PDMS known to the skilled person may be used.

Whilst there has been described in the foregoing description preferred embodiments of the present invention, it will be understood by those skilled in the technology concerned that many variations or modifications in details of design or construction may be made without departing from the present invention.

The invention claimed is:

1. An electrical contact comprising:
   (a) a top electrode comprising a non-Newtonian liquid metal alloy; and
   (b) a bottom electrode comprising a self-assembled monolayer of molecules (SAM) formed on a metal substrate, wherein the surface of the SAM layer of the bottom electrode contacting the top electrode is a template-stripped non-patterned surface and the electrical contact has no edge effect;
   and the surface of the liquid metal alloy contacting the SAM layer is contained in a polymer insulator and the area of the electrical contact between the liquid metal alloy surface and the SAM layer is determined by modulating the diameter of the liquid metal alloy surface contacting the SAM layer, the diameter being between 15 $\mu m$ and 55 $\mu m$.

2. The electrical contact according to claim 1, wherein the non-Newtonian liquid metal alloy is EGaIn.

3. The electrical contact according to claim 2, wherein the EGaIn contains 75.5 wt % Ga and 24.5 wt % In.

4. The electrical contact according to claim 1, wherein the polymer insulator is PDMS.

5. The electrical contact according to claim 4, wherein the PDMS is transparent.

6. The electrical contact according to claim 1, wherein the metal of the metal substrate is selected from the group consisting of silver, copper, nickel, platinum, palladium, and gold.

7. The electrical contact according to claim 1, wherein the SAM layer is formed from a material of 99.9% purity.

8. The electrical contact according to claim 1, wherein the SAM layer has a thickness of 1 nm to 2 nm.

9. The electrical contact according to claim 1, wherein the SAM layer is formed of molecules of formula $S(CH_2)_{n-1}CH_3$, n being 10, 12, 14, 16, or 18.

10. A method for forming the electrical contact of claim 1, the method comprising:
    (a) providing the top electrode comprising the non-Newtonian liquid metal alloy;
    (b) preparing the bottom electrode by forming the self-assembled monolayer of molecules (SAM) on a metal substrate; and
    (c) contacting the liquid metal alloy of the top electrode with the surface of the SAM layer of the bottom electrode.

11. The method according to claim 10, wherein the non-Newtonian liquid metal alloy is EGaIn.

12. The method according to claim 11, wherein the EGaIn contains 75.5 wt % Ga and 24.5 wt % In.

13. The method according to claim 10, wherein the polymer insulator is PDMS.

14. The method according to claim 13, wherein the PDMS is transparent.

15. An electrical contact comprising:
    a top electrode comprising a non-Newtonian liquid metal alloy; and
    a bottom electrode comprising a self-assembled monolayer of molecules (SAM) formed on a metal substrate, wherein the surface of the SAM layer of the bottom electrode contacting the top electrode is a template-stripped non-patterned surface and the electrical contact has no edge effect;
    and the surface of the liquid metal alloy contacting the SAM layer is contained in a polymer insulator and the area of the electrical contact between the liquid metal alloy surface and the SAM layer is determined by modulating the diameter of the liquid metal alloy surface contacting the SAM layer, the diameter being between 15 $\mu m$ and 55 $\mu m$; and the top electrode is prepared by stabilizing the non-Newtonian liquid metal alloy in a microfluidic device.

* * * * *